United States Patent [19]
Wood

[11] Patent Number: 5,896,983
[45] Date of Patent: Apr. 27, 1999

[54] PACKAGE DISPENSER FOR ONE OR MORE CONDOMS

[75] Inventor: Frederick Wood, Medford, N.Y.

[73] Assignee: Airtite Industries, New York, N.Y.

[21] Appl. No.: 08/959,353

[22] Filed: Oct. 28, 1997

Related U.S. Application Data

[63] Continuation-in-part of application No. 08/799,534, Feb. 12, 1997, Pat. No. 5,803,245, which is a continuation-in-part of application No. 08/502,926, Jul. 17, 1995, Pat. No. 5,662,214.

[51] Int. Cl.$^6$ ............................................. B65D 85/14
[52] U.S. Cl. ......................... 206/69; 128/844; 604/349; 206/278
[58] Field of Search ............................. 206/69, 278, 438; 128/844; 604/349; 223/111

[56] References Cited

U.S. PATENT DOCUMENTS

| | | | |
|---|---|---|---|
| 3,136,417 | 6/1964 | Clinch | 206/69 X |
| 3,469,685 | 9/1969 | Baermann | 206/306 |
| 4,638,790 | 1/1987 | Conway et al. | 604/349 X |
| 4,840,187 | 6/1989 | Brazier | 128/844 |
| 4,894,059 | 1/1990 | Larsen et al. | 604/349 |
| 4,917,113 | 4/1990 | Conway et al. | 128/844 |
| 4,961,734 | 10/1990 | Kassman | 604/349 |
| 5,117,841 | 6/1992 | McBath | 128/844 |
| 5,205,298 | 4/1993 | Hurst | 128/844 |
| 5,269,405 | 12/1993 | Wood | 206/69 |
| 5,456,354 | 10/1995 | Wood | 206/278 |
| 5,584,390 | 12/1996 | Wood | 206/278 |
| 5,662,214 | 9/1997 | Wood | 206/69 |

Primary Examiner—Bryon P. Gehman
Attorney, Agent, or Firm—Gottlieb, Rackman & Reisman, P.C.

[57] ABSTRACT

A package for dispensing one or more condoms directly on a penis. The package consists of a flexible container having the general configuration of a penis with a first leak proof layer inside with the open end of the layer stretched over the outside of the container. The layer has a strip for providing penetration or unsealing. The condom is located within the layer and the open end is rolled over the outside of the container and the leak proof layer. A second leak proof layer lines the inside of the condom with the open end rolled over the first leak proof layer and the condom. To dispense the condom on a penis, the penis is inserted and the strip is pulled to unseal the condom from the first layer, permitting the penis and the condom to be removed from the container.

6 Claims, 20 Drawing Sheets

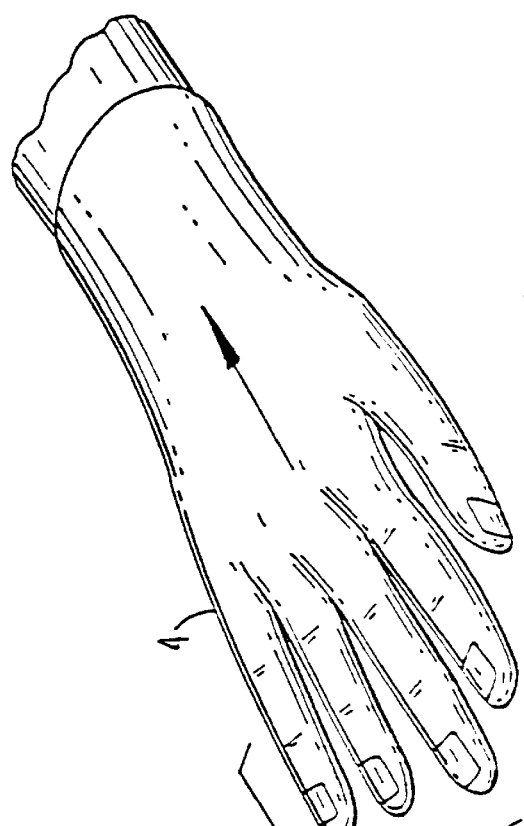
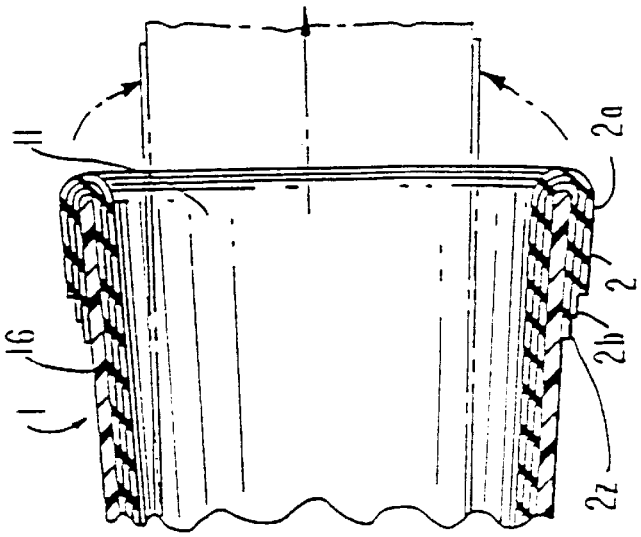
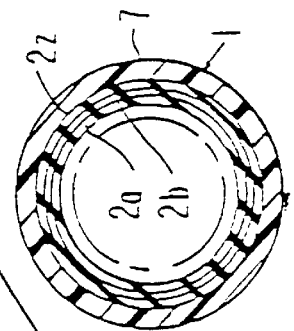
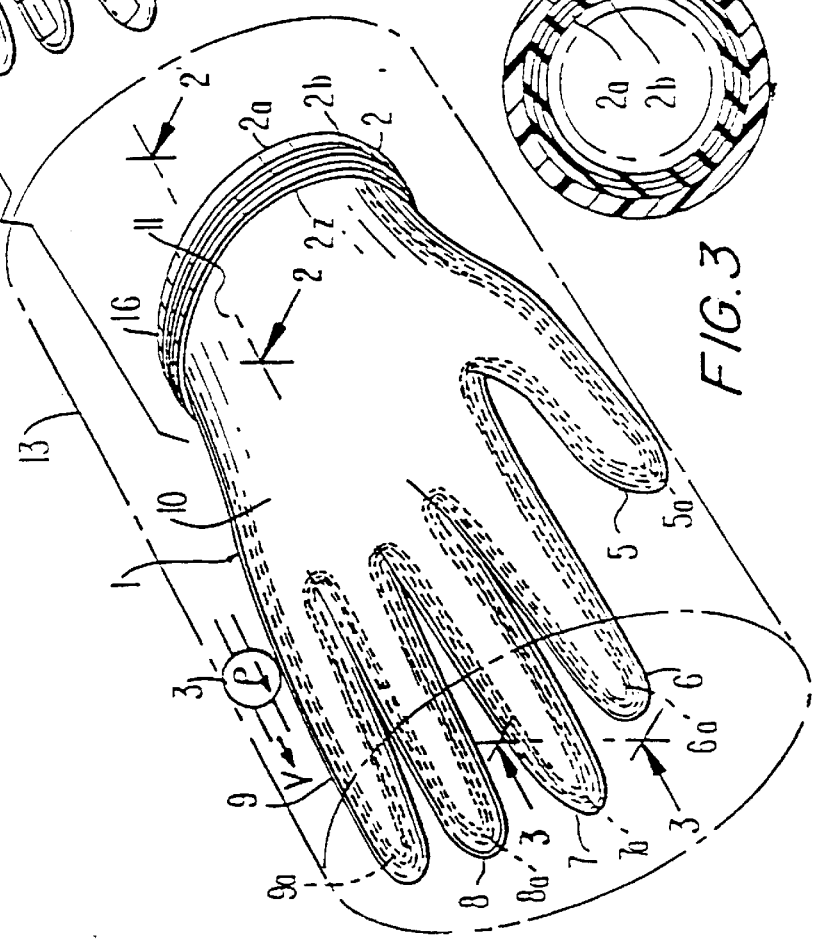

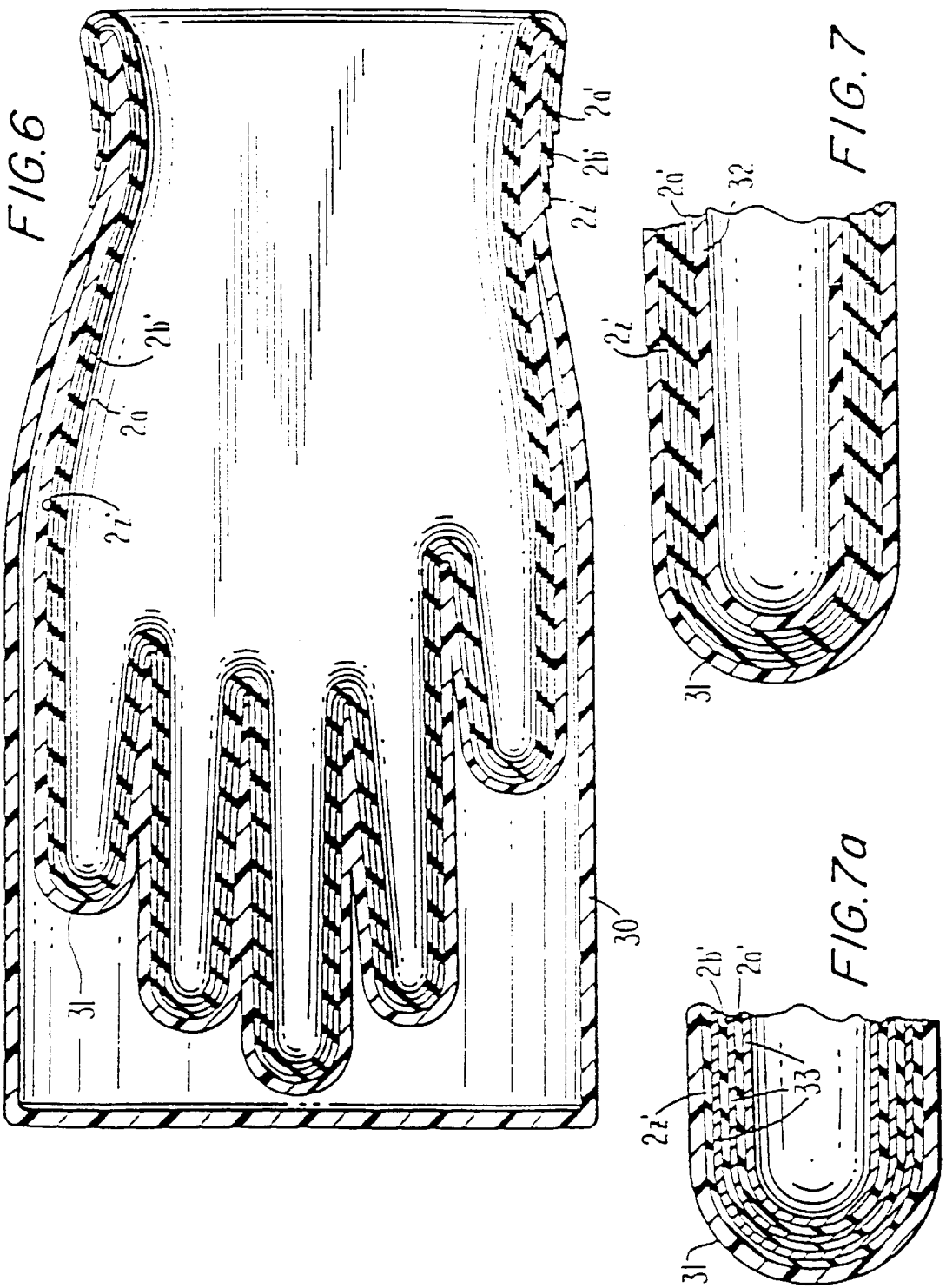

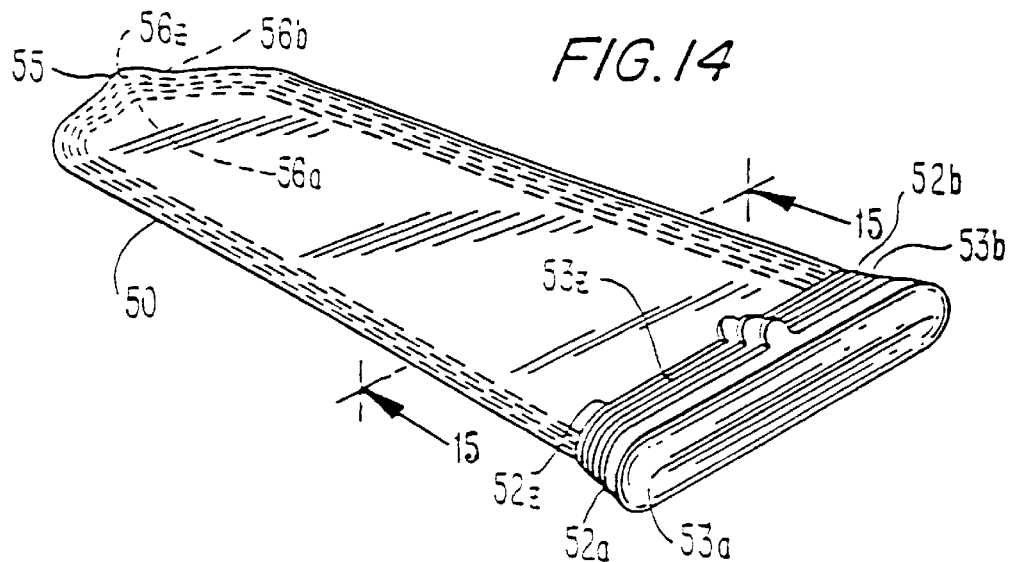
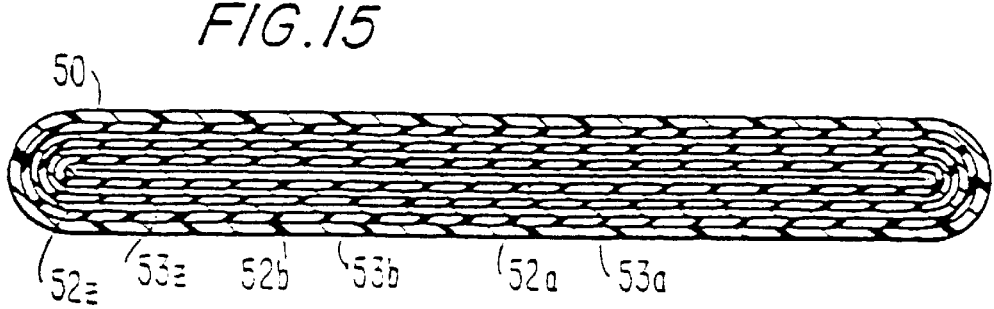
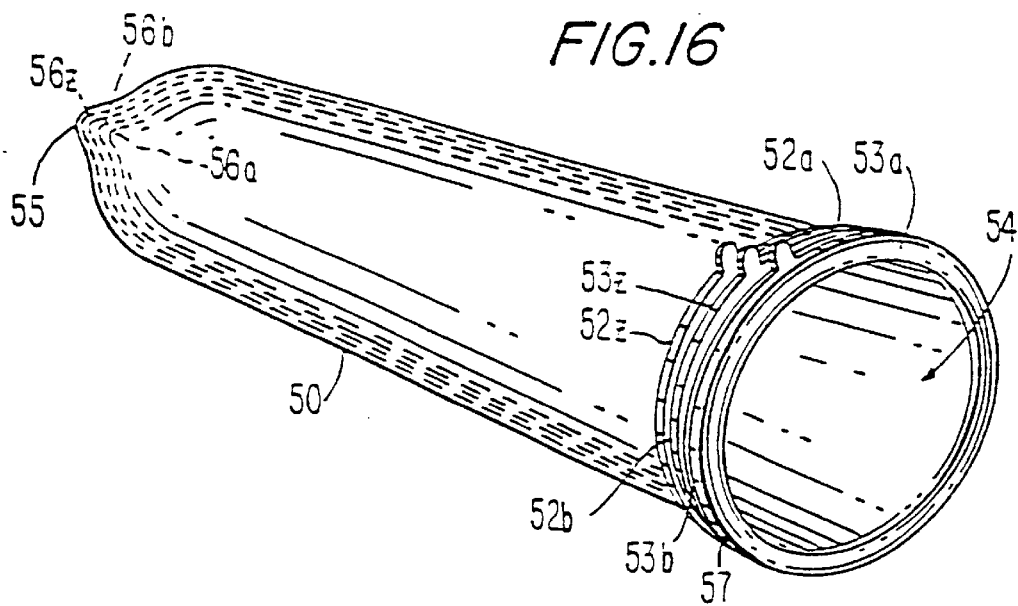

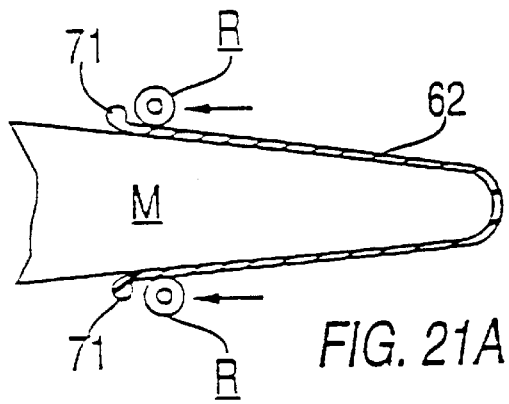
FIG. 21A
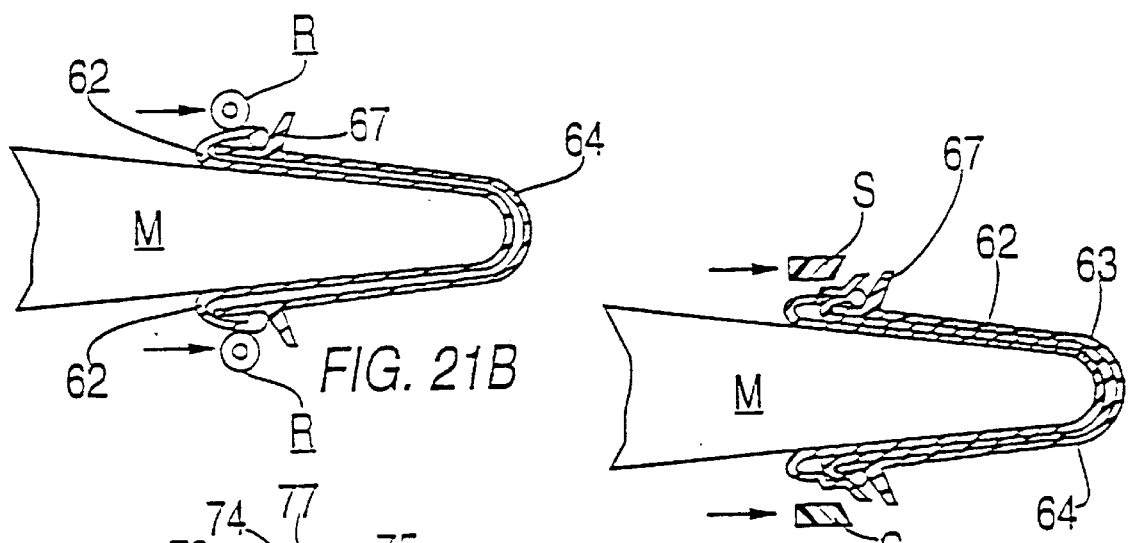
FIG. 21B
FIG. 21D
FIG. 21C
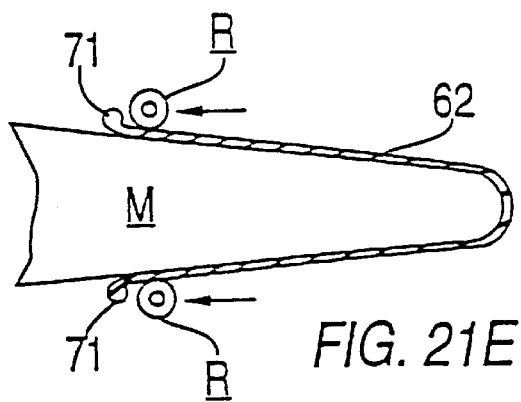
FIG. 21E

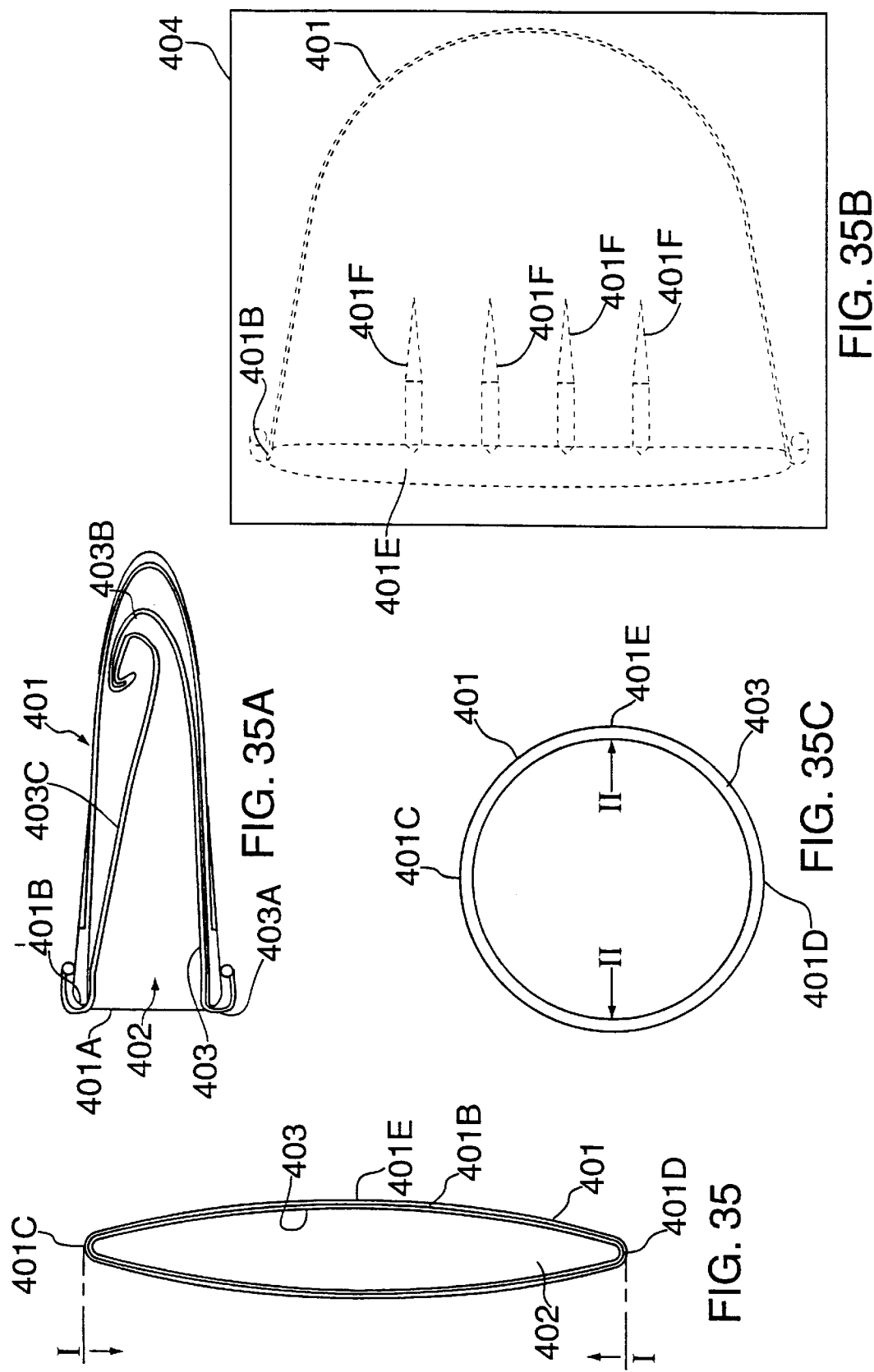

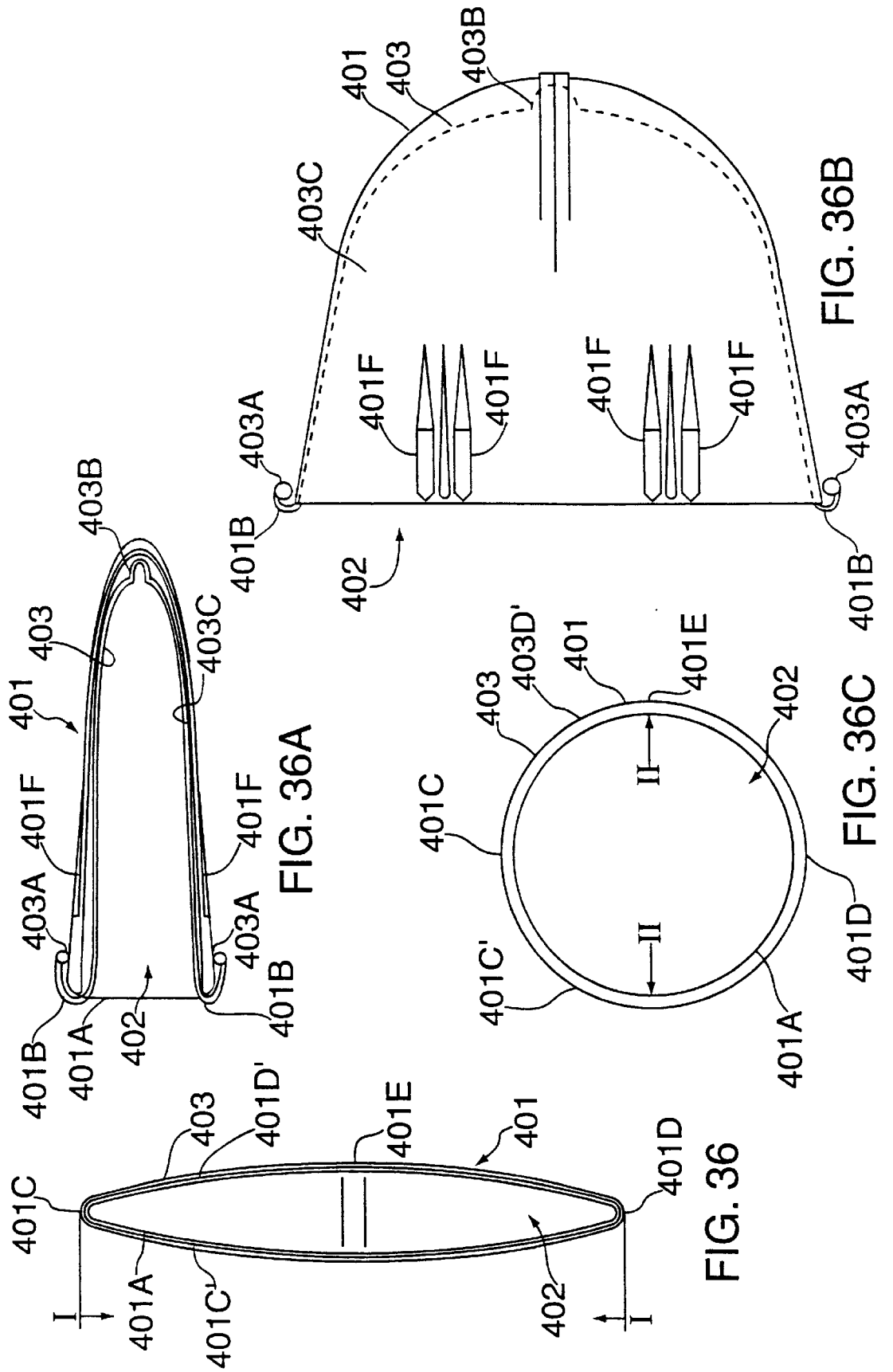

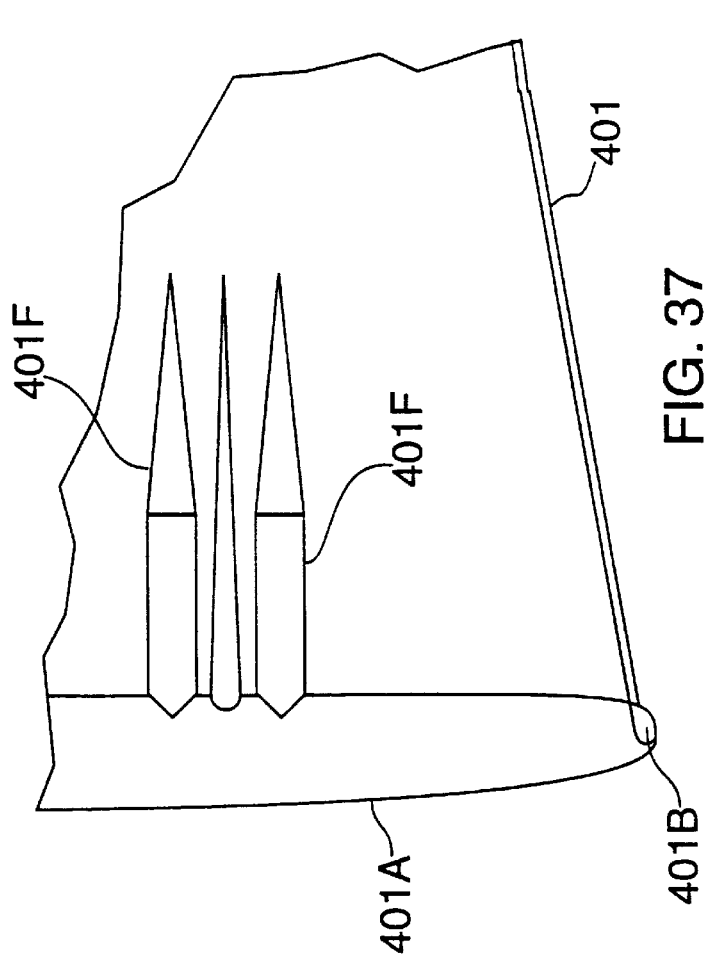
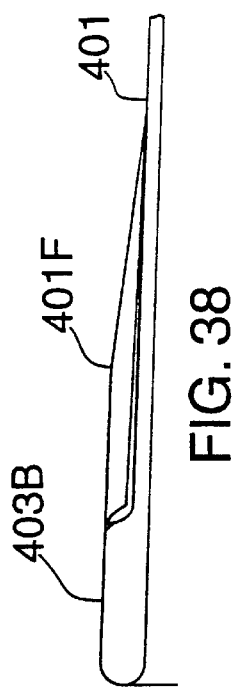
FIG. 37
FIG. 38

PACKAGE DISPENSER FOR ONE OR MORE CONDOMS

This application is a continuation-in-part of application Ser. No. 08/799,534, filed Feb. 12, 1997, now U.S. Pat. No. 5,803,245, which is a continuation-in-part of application Ser. No. 08/502,926, filed Jul. 17, 1995, now U.S. Pat. No. 5,662,214.

FIELD OF THE INVENTION

The present invention relates to a package dispenser for one or more elastic expandable garments, such as latex gloves or condoms. More particularly, the invention relates to a garment shaped package dispenser, wherein a user dons one or more garments sequentially from a garment-shaped container. For example the present invention may relate to a package dispenser for one or more condoms, wherein a user dons a condom from a container in the shape of a partially rolled condom. Each condom may be nested with one or more interleaved separators which form a hermetic seal around each condom.

BACKGROUND OF THE INVENTION

Among background art includes U.S. Pat. No. 4,840,187 of Brazier which describes a rigid, cylindrical tubular container to dispense rigid male urine collection sleeve, not a flattened closed container openable by pressing upon the side edges corresponding to the major axis of the open end of the container, as noted in the present invention.

The use of the flattened, openable container in the present invention would be discouraged, if not clearly taught away from the rigid cylindrical tubular container of Brazier '187.

Brazier '187 discloses a sheath applicator for directing a steam of urine. Thus the single sheath is open at the distal end and not closed as in a condom. In addition, the tubular casing does not conform to the shape of a condom, has a flexible liner casing which is exposed by side openings to permit adjustment of the flexible liner casing on the penis. Strip 12 therein is designed to expose an adhesive so when the sheath is rolled over the penis, the end of the sheath can be cemented to the base of the penis.

U.S. Pat. No. 4,696,095 of Elenteny has peel away multi-layered gloves which are peeled away one at a time. This arrangement is not suitable for use as a condom, as it lacks the leak proof layers in between the various layers of gloves.

Various devices have been made for releasing a single glove from a vacuum chamber. U.S. Pat. No. 5,269,405 of the Applicant describes a package for dispensing one or more gloves from a nested plurality of gloves, wherein a pump creates a vacuum to inflate the gloves in an open expanded state.

Applicant's U.S. Pat. No. 5,269,405 also discloses a container for sequentially dispensing a single glove from a plurality of gloves placed inside each other, wherein a vacuum holds the plurality of gloves intact in an open position for insertion of a hand therein.

Wood '405 discloses a dispenser for gloves which are stored in a layered condition within a container and a vacuum is applied. Each glove can be removed without disturbing the vacuum. Each glove has the open end pulled around the outside of the container with each succeeding glove layered on top of the preceding one.

Adhesive is employed to maintain a seal. To remove a glove the open edge of the glove is pulled away thereby relieving the vacuum surrounding the glove. The glove is pulled away thereby relieving the vacuum surrounding the glove to be removed, thus easing the removal of the glove. This is a far different arrangement from the present invention.

Applicant's U.S. Pat. No. 5,456,354 describes a package dispenser for garments such as one or more gloves or condoms, from a dispenser which is shaped like the garment to be dispensed. Among or other patents are U.S. Pat. Nos. 3,695,493 of Karr, disclosing an apparatus for alternately donning and removing a single glove within a vacuum chamber 4,069,913 of Harrigan for a package for donning a single surgical glove, and 4,889,266 of Wight for an apparatus which removes a single glove from a disposable single use package.

Other related patents include U.S. Pat. No. 685,574 of Conboie which shows a hand-shaped case, but for an unrelated use in mortuaries. The U.S. Pat. No. 1,938,685 to Breulis shows a somewhat bulb-shaped cavity for applying a surgical glove. The cuff of the glove is stretched over the opening of the cavity. The U.S. Pat. No. 2,741,410 to Violette shows a rack for removing gloves that may be wall mounted.

The U.S. Pat. No. 2,886,824 to Smith shows a rubber glove having a tapered wrist shape. The U.S. Pat. No. 3,852,826 to Schindler shows a surgical glove which is sterilized using radiation. The U.S. Pat. No. 4,186,445 to Stager shows a glove having a mylar outer coating and a polymer foam inner coating. The U.S. Pat. No. 4,310,928 to Joung and U.S. Pat. No. 4,851,266 to Momose show talc free surgical gloves. The U.S. Pat. No. 4,696,065 to Elenteny shows a single peel-away multi-layer glove. No powder is used between the layers. This glove has a slight taper at the wrist portion.

The U.S. Pat. No. to Richardson, 5,224,221 describes a single glove which is two layers, one inside the other, with the space between them evacuated.

Various devices have been made for packaging condoms. U.S. Pat. No. 5,269,405 of the Applicant herein describes a package for a plurality of condoms, wherein the condoms are nested within a tubular package having an open end and a closed end, wherein a pump creates a vacuum to inflate the condoms in an open inflated state. Applicant's U.S. Pat. No. 5,456,354, noted above, describes a package for a plurality of condoms which specifically describes a removable layer between each of the condoms, to maintain each of the condoms sanitary before use.

Among prior art patents related to condom manufacturing are U.S. Pat. No. 5,136,825 of White for an apparatus and method for compacting condoms in a pleated package and U.S. Pat. No. 4, 867,176 of Lash for a vacuum formed package for a female condom, as shown in FIG. 16 therein.

U.S. Pat. No. 4,638,790 of Conway describes a rolled condom which is adhesively adhered to the skin of a male user.

U.S. Pat. No. 5,316,019 of Jones described an annular applicator which functions as a package for a condom.

U.S. Pat. No. 5,267,575 of Hrisko describes a dispenser for an individual condom, wherein the condom is inflated before each use by blowing air through the dispenser to inflate the condom before donning. However, Hrisko '575 only describes an applicator for single condom, which must be inflated by the user blowing air into the dispenser before each use.

U.S. Pat. No. 4,987,905 of Broad describes a "no hands" application for a condom, wherein a pair of strips are moved to release the condom.

However, none of the above patents for donning condoms disclose an apparatus for donning one of a plurality of hermetically sealed condoms within a condom shaped chamber. As defined in the *Academic Press Dictionary of Science and Technology,* Publishers, ed. C. Morris, 1992 edition, at page 1015, a "hermetic seal" is defined as a seal that is impervious to air and other fluids, i.e. made airtight.

The United States Department of Health, Food and Drug Administration (FDA) mandates that condoms be manufactured to prevent pregnancy and to prevent the transmission of sexually transmitted diseases (STD's), from the mixture of bodily fluids between sexually active persons.

Pursuant to Title 21 U. S. Code, Section 360(c) (a) (1), FDA regulations classify medical devices in a hierarchy of classification standards, namely, Class I for medical devices which require general controls in manufacturing, Class II for medical devices which also require performance tests, and Class III, for medical devices which require FDA pre-market approval.

The FDA has classified the condom as a Class II device under 21 CFR 884.5300. The condom must be subject to rigorous performance tests, such as air burst tests, to certify that the condoms are sealed from leakage.

The FDA utilizes the manufacturer's standards of the American Society for Testing Materials (ASTM) entitled "Standard Specification for Rubber Contraceptives" (Condoms)[11]—Designation: D 3492-83 for quality control of leakage defects, wherein the acceptable quality level for leakage is 0.4 percent, that is, not to exceed 4 leaking condoms per 1000 is tested. The FDA's sampling inspections, pursuant to 21 CFR 800.20, are based on the tables of MIL - STD - 105 E which is the military sampling standards in "Sampling Procedure and Tables for Inspection by Attributes", dated May 10, 1989.

Among the tests for condoms include the Air Inflation Test, adopted in 1994 by U. S. inspectors, which includes inflating condoms, checking their elasticity, whereby experts determine the quality that keeps a condom intact during intercourse.

As noted in "How Reliable Are Condoms?" Consumer Reports, May 1995, pp 320–324, latex condoms are produced by dipping a cylindrical form in liquid latex and heating it. Machines shape and trim the condoms ring; then new condoms are washed and aged for a number of days, during a "curing" that lets the rubber complete the chemical actions that strengthen the latex. The final steps are rolling and wrapping individual condoms.

Industry standards require a width of no greater than 54 millimeters,—about 2⅛ inches, to prevent slippage. The minimum length is 160 mm, roughly 6⅓ inches.

Since 1987, the U.S. Food and Drug Administration has allowed condom boxes to list all the diseases condoms help avert.. More recently, the FDA advised a condom manufacturing company that because the disease-prevention message is so important, manufacturers should also print a disease prevention message on the wrappers of individual condoms.

Therefore, both manufacturers and the FDA take steps to catch the flawed condoms before they can leave the factory.

OBJECTS OF THE INVENTION

It is an object of the present invention to provide a disposable dispenser for a single use condom.

It is another object of the present invention to provide a garment package dispenser which has an inner shape which constricts the palm and forces the fingers of the garment to expand and conform to the proper position to allow easy donning.

It is therefore a further object of the present invention to provide a package dispenser for dispensing one or more garments sequentially from a glove-shaped vacuum container.

It is yet another object of the present invention to provide a garment dispenser that allows powderless gloves to be easily donned.

It is a further object to provide a garment-shaped package with a releasing means including a thin continuous ribbon.

It is a still further object to provide a garment-shaped package with a releasing means including a thin ribbon for each garment.

It is yet another object to provide a garment package with an annular releasing means.

It is yet another object to provide a garment package with a releasing means including a tubular plastic cover which has a wasted area line cut spiraling around it so when the tab is removed it resembles a spiral shape.

It is yet another object to provide a container with a neck opening of a garment package which is tapered inward so that when the plastic is pulled off, the cuff of the garment easily rolls off the package and onto the hand.

It is a further object to provide a garment package dispenser in the shape of a large hand for a glove.

It is yet another object of the present invention to provide a glove dispenser for powder free gloves.

It is another object to provide a surgical glove package dispenser which provides a fast method of donning surgical gloves.

It is a further object to provide a surgical glove dispenser with a single wall container shaped like a large glove.

It is yet another object to provide a single or double walled glove package container with the inside shaped like a large glove and the outside having a box-like shape.

It is a further object to provide a glove package dispenser with a regular box-like shaped exterior and a flexible non-elastic large glove shape inside.

It is a further object to provide a glove package dispenser which is flattened for convenient storage and has a flexible non-elastic large glove shape inside.

It is yet another object to provide a glove package wherein the gloves in the package are stored in a relaxed shape, so that when the package is opened for use, the vacuum in the hollow tip causes a plurality of gloves to expand into the proper shape.

It is yet another object to provide a glove dispenser wherein an inner glove component which has holes in it to release trapped air.

It is yet another object to provide a garment dispenser which includes a flexible non-elastic garment shape on the inside of the plurality of garments which is sealed within package in order to provide a leak-proof, air free area for increased shelf-life or storage life of the garments.

It is yet another object to provide a leak-proof layer in between each garment.

It is yet another object to provide a plurality of garments wherein there is provided an outermost garment shape which constitutes a leak-proof layer, for the purpose of shaping all the garments.

It is yet another object to provide a garment package with an opening which is flared out to prevent unwanted releasing of the garments.

It is yet another object to provide a garment dispenser package with an opening which is tapered in to aid in the releasing of each garment.

It is yet another object to provide a garment package with a mechanical attachment for pulling a release tab, to allow for hands-free or automatic releasing of the garments.

It is an object of the present invention to provide a condom or condom package dispenser which has an inner shape which forces a condom to expand and conform to the proper position to allow easy donning.

It is also an object of the present invention to provide a dispenser for dispensing one or more condoms, or packages of condoms, sequentially from a container.

It is a further object to provide a condom shaped package dispenser with a releasing means.

It is a still further object to provide a condom-shaped package dispenser with a hermetically sealed layer between each condom.

It is another object to provide a dispenser which permits a conveniently hands-free method of donning condoms.

It is a further object to provide a condom package dispenser which is flattened for convenient storage.

It is yet another object to provide a condom package dispenser wherein the condoms in the package are stored in a relaxed shape, so that when the dispenser is opened for use, the partial vacuum in the hollow tip causes the plurality of condoms to expand into the proper shape.

It is yet another object to provide a dispenser with a neck opening which is flattened so that when the neck opening is squeezed, a partial vacuum is formed by the increase of volume within the closed interior of the condom shaped dispenser.

It is yet another object to provide a condom package dispenser with a leak-proof layer in between each condom.

It is also an object of the present invention to improve over the disadvantages of the prior art.

SUMMARY OF THE INVENTION

In keeping with these objects and others which will become apparent, the present invention includes a garment-shaped container package dispenser for sequentially dispensing at least one elastic expandable garment, such as a single condom or a plurality of condoms.

In the preferred embodiment, a package dispenses one or more condoms directly on a penis. The package includes a flexible pouch container having the general configuration of a penis. An optional interior plate, within the container prevents the condom from shrinking away from the outside walls of the container.

In another embodiment for gloves, such as latex surgical gloves or the like, the gloves are maintained in an open, expanded state, wherein the user loosely inserts a hand into the innermost glove, breaks the air seal by pulling a tab or similar device, thus allowing air to leak in around the innermost glove, so that the glove snaps over the hand of the user in a tight fitting manner.

The remaining gloves stay in an expanded state, so that if the user desires to wear two or more gloves, the user then releases a tab to break the seal against the next, exposed, innermost glove, whereupon the next innermost glove snaps into place over the previous first innermost glove upon the hand of the user.

The inside of the package dispenser container of another embodiment for dispensing gloves is glove-shaped, so that the gloves may be expanded in the proper state and condition. Otherwise, in a non-descript tubular or box-like package, the finger portions will not expand or they will become distorted when forced to expand and will not be held in a useful shape, thus necessitating the use of powder to lubricate the finger portions.

In comparison, the glove-shaped package dispenser of the present invention permits proper expansion of all surfaces of the glove, including the fingers, thus obviating the need for powder as a lubricant.

To release a garment, such as a glove or a condom, the releasing means may be a thin continuous ribbon made out of latex or plastic, wherein the user pulls a predetermined length of the tab to release the glove or condom. Alternatively, the releasing means may be a tubular plastic cover, with a wasted line cut in an annular fashion, or spiraling around the cover, so that as it is removed the releasing means resembles a large spring or spiral shape. In one embodiment, the neck of the hand-shaped glove package is tapered inward, so that when the plastic releasing means is pulled off, the cuff end of the innermost glove is separated from the package and onto the hand of the user.

With respect to the glove-shape of the glove package dispenser, several variations are described herein. For example, the inside and/or the outside of the package may be in the shape of a large glove.

Moreover, a conventional tubular or box-like package dispenser container may be used, wherein the inner glove-shape is achieved by having an outermost glove shape layer, made of a non-elastic plastic hand-shaped material, such as Mylar®.

The glove-shaped package dispenser container also allows the user to quickly put on the gloves in exigent circumstances, such as in an ambulance or for police use.

The glove-shaped package dispenser container,. or similar modifications, obviates the need for powder to slide the glove on the hand of the user. The powder, which is presently used on latex gloves, causes problems, such as irritation of the eyes and skin. The powder may also cause allergic respiratory ailments. Moreover, hand perspiration causes the powder to become caked on, making it difficult to wash off. In addition, powder can contaminate surgical incisions, so a surgeon must carefully remove the powder with a sterile towel before surgery, which is a time consuming step.

In order to easily don gloves without powder, the glove-shape of the package dispenser constricts the palm portion of the glove and forces the fingers of the glove to expand and conform to the proper position to allow easy donning.

To release any trapped air, the inner glove shape mentioned in the above designs may have holes in it.

It is anticipated that the gloves are to be dispensed in disposable or refillable cartridges of a number of gloves, such as, for example, two dozen. The cartridges are held in a mounting means, such as upon a wall.

In order to hold the glove cartridge firmly in the holder the glove cartridge may have one or more female snaps on the top or one side of it which mate with male snaps on the inside of the glove cartridge holder. This allows for the recognition of different glove sizes and prevents the glove cartridges from being installed in a wrong location, thus, in turn, preventing the donning of the wrong sized glove upon the hand of the user.

In another embodiment for dispensing elastic expandable garments from a package, the package dispenser container of the present invention may also be used for donning condoms from a condom-shaped package which folds flat for storage. In the case of the condom package, where the garments would not be used up as fast as gloves, there may be a special leak-proof layer in between each condom. This would also provide extra cleanliness for the inside of the innermost condom that would otherwise be exposed to the outside air.

For non-surgical, non-elastic gloves, the gloves may be stacked and packaged without a vacuum if they are designed with a tapered shape so that the innermost glove(s) do not get crushed. These gloves have no air in between the layers. The wrist part of these gloves is the largest part, tapering down to the fingertips, wherein the gloves have an integral release tab which gets exposed only when the innermost glove inside of it has been removed.

In summary, the present invention relates to a package dispenser for one or more garments such as a condom or a surgical glove. More particularly, the present invention relates to a garment-shaped package dispenser, wherein a user dons one or more garments sequentially from a vacuum packed garment-shaped container. In a preferred embodiment, the shape of the package allows even powder free gloves to be donned quickly and easily, because the inner hand shape constricts the palm of the glove and forces the fingers to expand and conform to the proper position within the package interior.

The present invention also includes a condom-shaped package dispenser for sequentially dispensing at least one elastic expandable condom, from a dispenser package.

In the preferred embodiment, the condom is preferably nested within the package and is maintained in the package in a flattened, partially unrolled state. The user squeezes the flattened package to open the openable end, breaks an air tight seal by pulling a tab or similar device, thus releasing an air tight layer from around the condom, so that the condom is opened for donning when the condom dispenser is inserted over the skin of the male for use. One advantage of this embodiment is that the user is not able to mistakingly don the condon inside out.

In another embodiment, one condom is dispensed from a plurality of condoms and the remaining condoms remain in an open state, so that when the user desires to use a condom at a later time, the user then releases a tab to release a next innermost seal from against the next innermost condom, whereupon the next innermost condom is available for use.

The inside of the condom package dispenser of the preferred embodiment is condom-shaped, so that the condom may be expanded in the proper state and condition.

Another embodiment provides a plurality of individually sealed single condom packages in a partially unrolled state to facilicate donning, which packages are removable from each other by a tear seal.

In summary, the inside of the package dispenser for dispensing one or more condoms is condom-shaped. The package dispenser folds flat for storage. There may be a hermetically sealed leak-proof layer in between each condom. This provides extra cleanliness for the inside of the innermost condom that would otherwise be exposed to the outside air. The user dons one or more condoms sequentially from the condom-shaped container. The shape of the dispenser allows condoms to be donned quickly and easily, because the condom shape, when squeezed at the open neck end, forces the condoms to expand and conform to the proper position within the interior of the dispenser.

DESCRIPTION OF THE INVENTION

The invention can best be understood from the specification and drawings, in which:

FIG. 1 is a perspective view of one embodiment of the glove package dispenser of the present invention.

FIG. 2 is a blown-up cross-sectional view of the glove package dispenser as in FIG. 1, taken along line 2—2 of FIG. 1.

FIG. 3 is a blown-up cross-sectional view of the glove package dispenser as in FIG. 1, taken along line 3—3 of FIG. 1.

FIG. 6 is a side-sectional view of a third embodiment of a glove package dispenser.

FIG. 7 is a blown-up sectional view of the glove package dispenser as in FIG. 6.

FIG. 7A is a blown-up sectional view of an alternate embodiment of the glove dispenser package.

FIG. 14 is a perspective view of a condom dispenser embodiment of the present invention, shown in a closed position.

FIG. 15 is a blown-up cross-sectional view of the condom dispenser embodiment as in FIG. 14, taken along lines 15—15 of FIG. 14.

FIG. 16 is a perspective view of the condom dispenser embodiment as shown in FIG. 14, shown in an open position.

FIGS. 35 and 35C are respective front views of a further embodiment for an openable pouch package for a condom, wherein the package is shown closed and open.

FIG. 35A is a side elevational view in cross section of the pouch package as in FIG. 35; and FIG. 35B is a top plan view of the embodiment of FIG. 35A.

FIGS. 36, 36A, 36B and 36C show the pouch package of FIGS. 35, 35A, 35B and 35C with a condom therein.

FIGS. 37 and 38 are close-up views of the condom support members upon the pouch package as in FIGS. 35, 35A, 35B, 35C, 36, 36A, 36B, 36C and 36D.

DETAILED DESCRIPTION OF THE PREFERRED EMBODIMENTS

Figure 4:
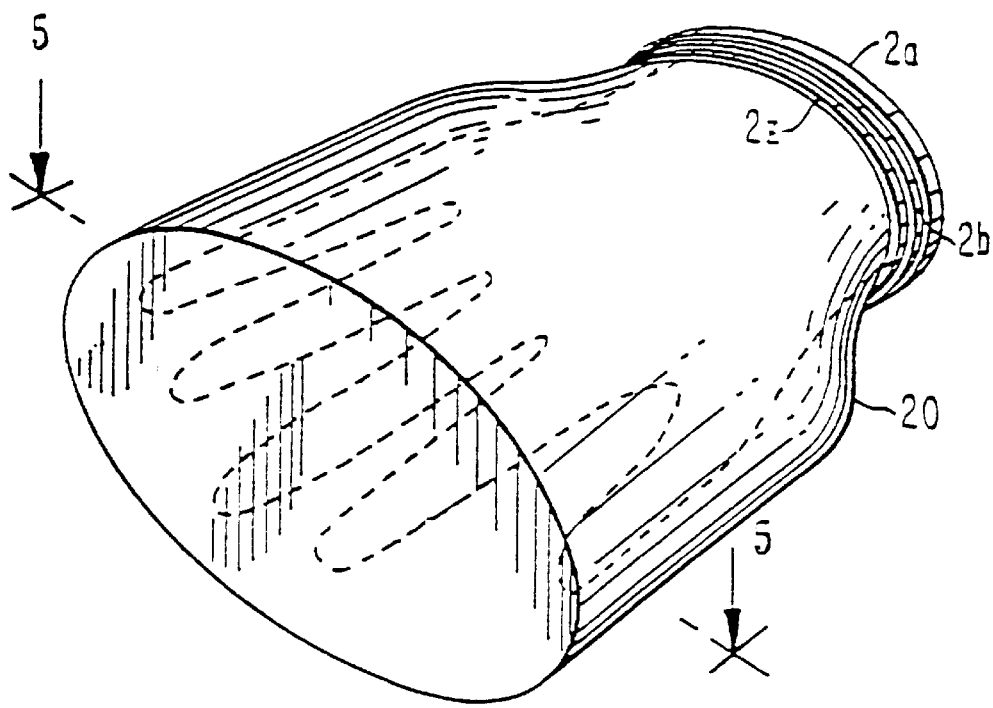
FIG. 4 is a perspective view of another embodiment of a glove package dispenser, wherein the inside surfaces of the package are a mirror image of a glove.

As shown in FIGS. 1–3, there is provided a package dispenser 1 for a plurality of elastic expandable garments such as glove 2, for donning upon a hand of a person, wherein package dispenser 1 comprises a glove shaped inner cavity 11 within a housing 13 shown in phantom wherein a user inserts a hand and dons at least one glove 2 of a plurality of gloves 2a, 2b, 2c, 2d, . . . 2z etc. sequentially from a vacuum packed accumulation of garments 2, which is subject to a vacuum pressure V, within the dispenser such as drawn by a pump 3 in the manufacturing process for loading package dispenser 1 with gloves 2a, 2b, 2c, 2d, . . . 2z etc. The vacuum pressure V within the dispenser unit 1 is sufficient to open fully and expand uniformly each of the gloves in the glove-shaped cavity 11 within the dispenser 1.

In a one embodiment, the glove shape of package dispenser 1 eliminates the need for powder on gloves 2, such as, for example, latex surgical gloves. Vacuum V is drawn away from external outermost glove 2z and remaining gloves 2a, 2b, 2c etc., thus expanding gloves 2a, 2b, 2c, 2d . . . 2z in an open position.

Glove package dispenser 1 operates to release innermost single glove 2a from the application of vacuum V within package dispenser 1, which package dispenser 1 functions as an apparatus for sequentially donning one or more glove upon a body part such as a hand 4 from a plurality of gloves 2a, 2b, etc.

Glove package dispenser 1 enables the user to sequentially don gloves 2a, 2b, . . . 2z etc. from the plurality of gloves 2 placed inside each other, wherein vacuum V holds the plurality of gloves 2 within the cavity 11 intact in an open position for insertion of the user's hand 4 therein.

Glove-shaped package 1, includes palm portion 10 and individual finger portions 5, 6, 7, 8, 9 to maintain equal expansion of all surfaces of glove 2, so that, for example, five finger portions 5a, 6a, 7a, 8a, 9a of glove 2a are held in the proper expanded open position, thereby obviating the need for powder to lubricate gloves 2a, 2b, 2c etc.

The cuffs of the gloves 2a, 2b, 2c, 2d . . . 2z etc. are stretched over the collar portion 16 of the open end of the inner cavity 11 of the glove package dispenser 1 by virtue of which the open end of the gloves 2a, 2b, 2c . . . 2z etc. are maintained in an open, expanded state, permitting the user to insert a hand 4 into innermost glove 2a.

Figure 11:
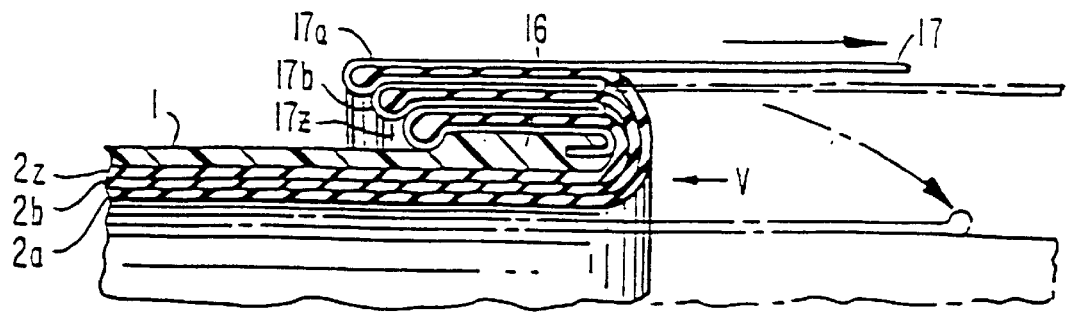
FIG. 11 is a blown-up sectional view of one embodiment for a release tab portion of the glove package dispenser.

As shown in FIG. 11, after insertion of a hand 4, the user breaks a seal by pulling a first portion 17a of seal tab 17 or similar device, such as a thin continuous ribbon made out of latex or plastic. The user pulls first portion 17a of a predetermined length of tab 17 to relieve innermost glove 2a from vacuum V, so that glove 2a is released from the next, subsequent innermost glove 2b, and glove 2a then snaps over the hand 4 of the user in an air tight manner.

Remaining gloves 2b, 2c, 2d . . . 2z etc. stay in an expanded state, so that if the user desires to wear two or more gloves 2 on one hand, the user then releases a further portion 17b of seal tab 17 from the next, exposed, innermost glove 2b, whereupon the next innermost glove 2b snaps into place over the previous first innermost glove 2a upon the hand 4 of the user. Ultimately, the user dons the remaining outermost glove 2z by pulling the last remaining portion 17z of release pull tab 17, to release outermost glove 2z from its open expanded state under the influence of vacuum V.

Figure 12:
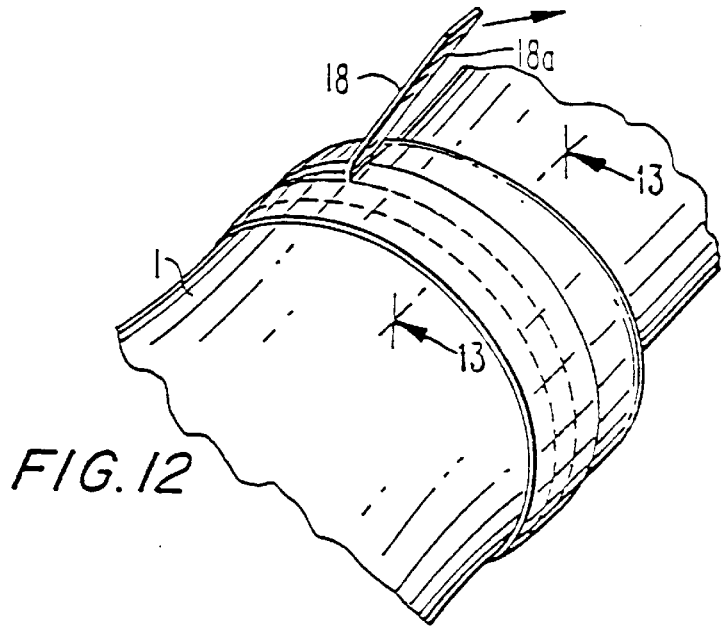
FIG. 12 is a blown-up perspective view of another embodiment for a release tab portion of the glove package dispenser.
Figure 13:
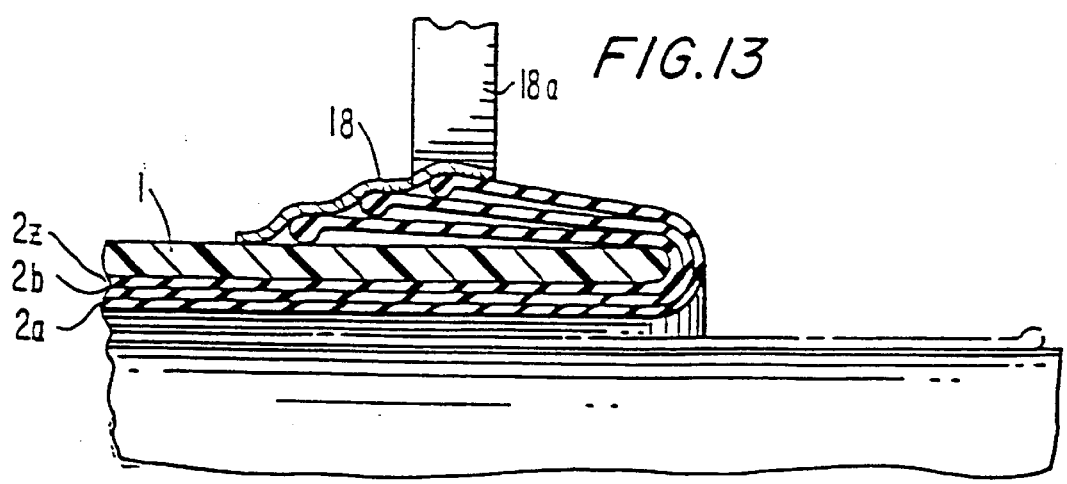
FIG. 13 is a blown-up cross-sectional view of the release tab as in FIG. 12, taken along lines 13—13 of FIG. 12.

In contrast to the release tab embodiment shown in FIG. 11, alternatively, as shown in FIGS. 12 and 13, the releasing means may be a tubular plastic cover 18, with a wasted linear area cut spiraling around the cover so that as it is removed, releasing portion 18a of release cover 18 resembles a large spring or spiral shape.

Glove package dispensing container 1 of the present invention is glove-shaped, to maintain equal expansion of all of the surfaces of gloves 2. Otherwise, in a non-descript tubular or box-like package, equal expansion is not maintained in the crevices and undulating finger portions 5, 6, 7, 8, 9 of glove 2, thus necessitating the use of powder to lubricate the finger portions and allow donning.

The glove-shaped dispenser package 1 of the present invention, as indicated, permits an equal expansion of all surfaces of glove 2, including palm portion 10 and finger portions 5, 6, 7, 8, 9, thus obviating the need for powder to lubricate the glove 2, to allow the user's hand to be readily inserted within the latex glove.

In one embodiment, collar neck 16 of the open end of the glove-shaped package dispenser 1 may be tapered inward, so that when the plastic releasing means 17 or 18 is pulled off, the cuff end of the innermost glove 2a is separated from the package 1 and onto the hand 4 of the user.

Figure 5:
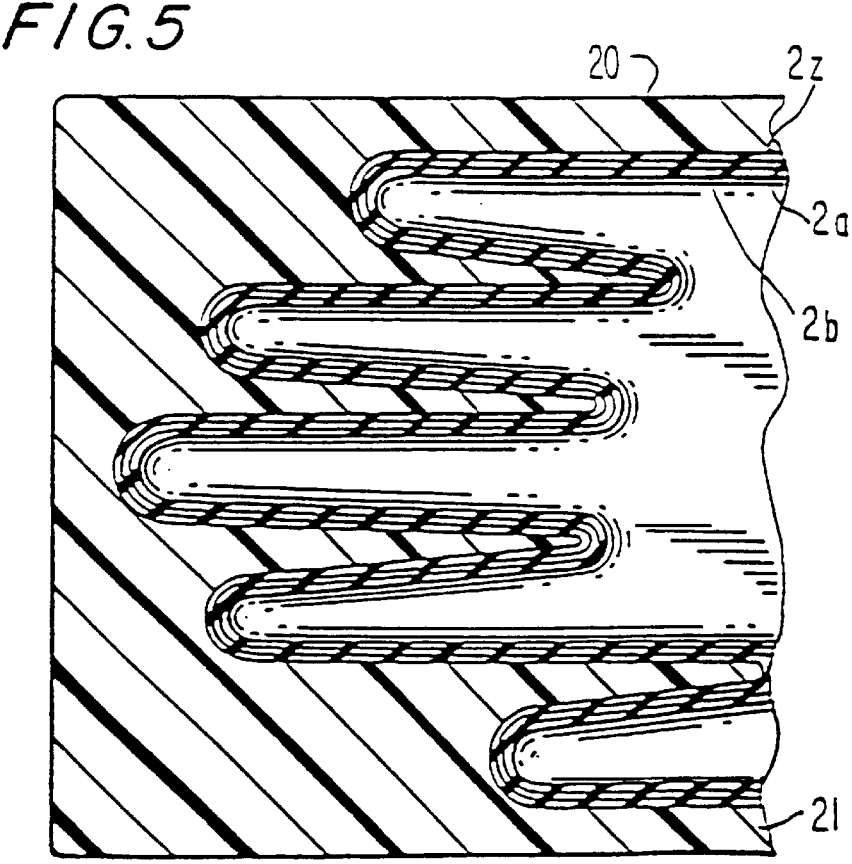
FIG. 5 is a blown-up cross-sectional view of the glove package dispenser as in FIG. 4, taken along lines 5—5 of FIG. 4.

With respect to the glove-shape feature of the glove package dispenser, several variations are described herein. For example, as shown in FIGS. 4 and 5, the inside 21 of a package 20 may be solid surrounding the shape of a large glove shaped cavity 11 with adequate means therein for drawing a vacuum.

Moreover, as shown in FIGS. 6 and 7, a conventional hollow container 30 may be used, such as a tubular container or a box-like container, wherein the glove-shape cavity 11 is achieved by having an outermost inelastic glove-like layer 31 positioned adjacent to and about outermost glove 2z' of gloves 2a', 2b' . . . 2z', wherein inelastic layer 31 is made of an inelastic gas impermeable plastic hand-shaped material, such as non-elastic Mylar®.

Therefore, gloves 2a', 2b' . . . 2z' will expand equally inside of each other in an expanded state against inelastic glove-like layer 31, due to the effect of vacuum V initiated by pump 3 (not shown) when gloves 2a', 2b, 2c' . . . etc. 2z' are installed in an expanded state against inelastic gas impermeable layer 31 within container 30.

As shown in FIG. 7, if there is a significant time delay before innermost glove 2a' is used, a special preferably gas impermeable protective layer 32 is provided inside of innermost glove 2a'.

As shown in FIG.. 7A an innermost protective layer 33 is provided inside innermost glove 2a'. Thereafter internal protective layers 33 preferably gas impermeable are provided between each glove of gloves 2a', 2b' . . . 2z' until outermost glove shield layer 31 such as Mylar®.

In order to easily don gloves without powder, the glove-shape of the package 1 constricts palm portion 10 of each glove 2 and forces fingers 5, 6, 7, 8 and 9 of glove 2 to expand and conform to the proper position to allow easy donning upon the hand 4 of the user.

To release any trapped air, the inner glove shape mentioned in the above designs may have holes in it.

The gloves 2 are dispensed in disposable or refillable glove-shaped cartridges 1 including therein a plurality of gloves 2, such as two dozen. In use package dispenser cartridges 1 are held in a mounting means, such as upon a wall.

In order to hold glove cartridge package dispenser 1 firmly in a holder the glove dispenser cartridge 1 may have one or more female snaps located on the top or one side of the package dispenser which mate with male snaps on the inside of the glove cartridge holder. This allows for the recognition of different glove sizes and prevents the glove dispenser cartridges from being installed incorrectly.

Figure 8:
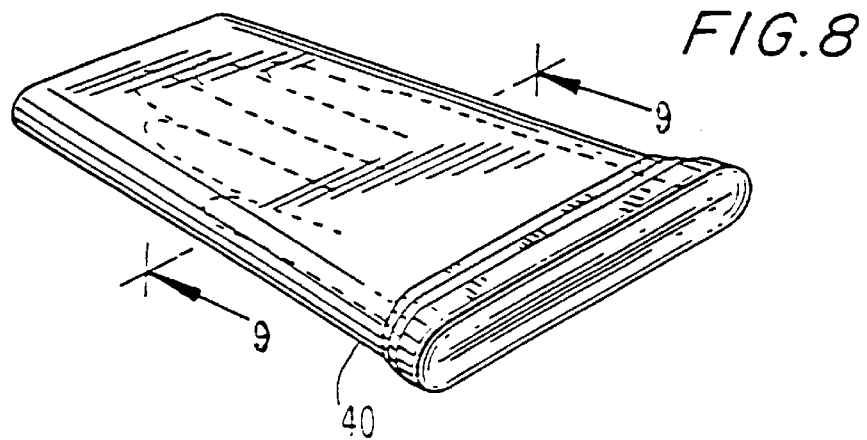
FIG. 8 is a perspective view of a fourth embodiment of a glove package dispenser, shown in a closed position.
Figure 9:
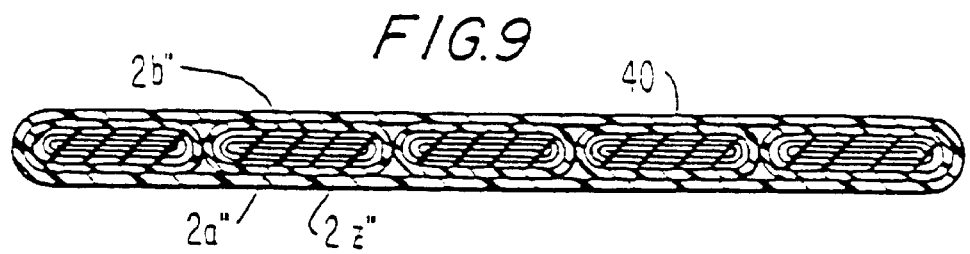
FIG. 9 is a blown-up cross-sectional view of the glove package dispenser as in FIG. 8, taken along lines 9—9 of FIG. 8.
Figure 10:
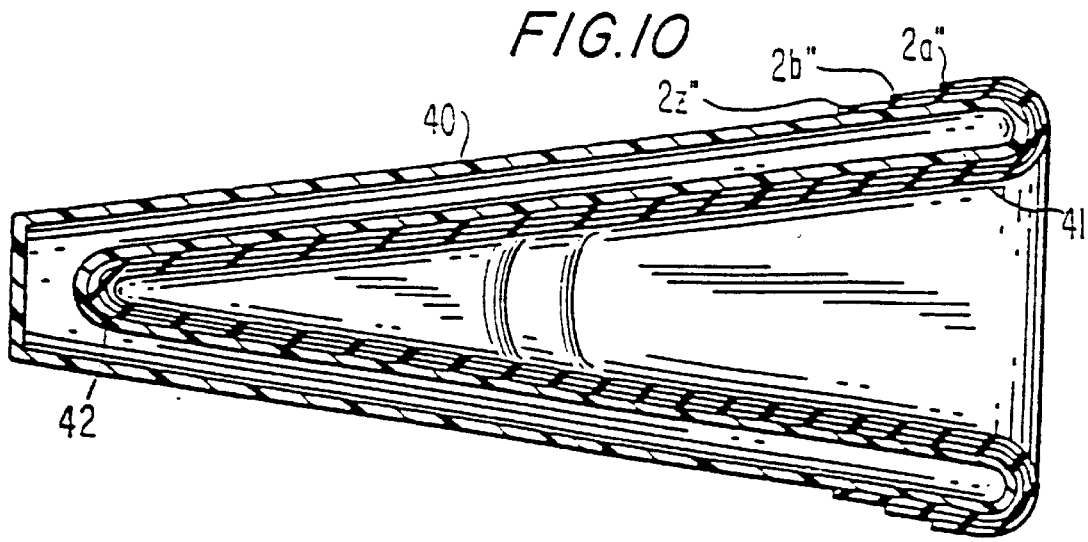
FIG. 10 is a blown-up cross-sectional side elevational view of the glove package dispenser as in FIG. 8, shown in an open position.

As shown in FIGS. 8–10, in an alternate embodiment of a package dispenser 40 for gloves 2a", 2b", 2c", 2d", etc., the gloves may be stacked and packaged within the dispenser package without a vacuum if they are designed with a tapered shape so that innermost gloves 2a", 2b", etc. do not get crushed. These gloves 2a", 2b", etc. have no air in between the layers. The wrist part 41 of these gloves 2a", 2b", etc. is the largest part, tapering down to the fingertips 42, wherein the gloves 2a", 2b", etc. have an integral release tab which is exposed only when the innermost glove inside of it has been removed.

Therefore, glove shaped package dispenser 1 allows a user to don one or more gloves sequentially from a vacuum packed hand-shaped container. In a preferred embodiment, the shape of the container will obviate the need for powder on latex gloves.

As shown in FIGS. 14–16, in another embodiment of the package dispenser for elastic, expandable garments, the container of the present invention may also be used for donning elastic, expandable condoms from a condom-shaped package 50, which folds flat for storage. In the case of condom package 50, where condoms 52a, 52b . . . 52z etc. would not be used up as fast as gloves, there may be provided a special protective leak-proof layer 53a, 53b . . . 53z inside of innermost condom 52a, and subsequent protective layers 53b . . . 53z in between each of the condoms 52b . . . 52z etc. This feature provides extra cleanliness for the inside of each condom 52a, 52b . . . 52z etc. One advantage of this embodiment is that the user is not able to mistakingly don the condon inside out because it is partially unrolled in the correct position for donning.

Figure 17:
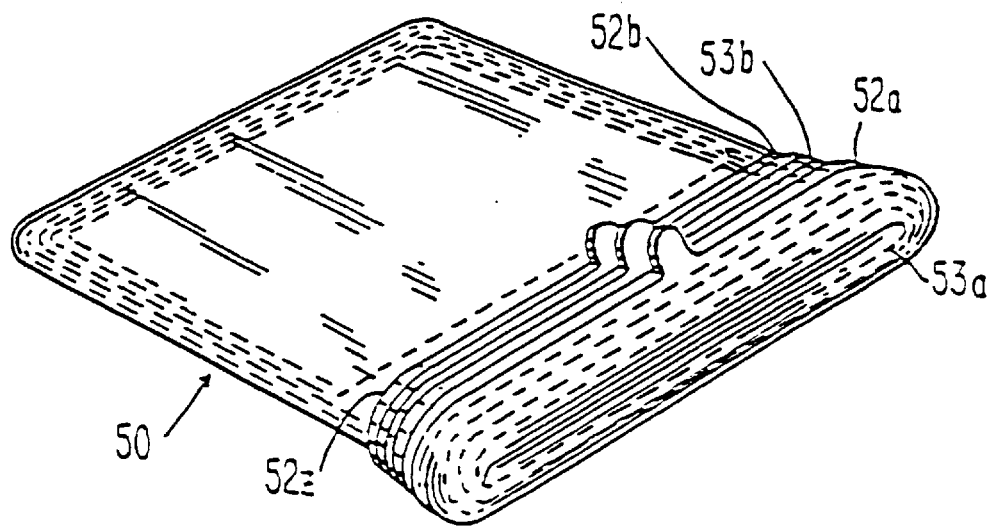
FIG. 17 is a perspective view of an alternate embodiment of a condom dispenser, shown in a closed position.
Figure 18:
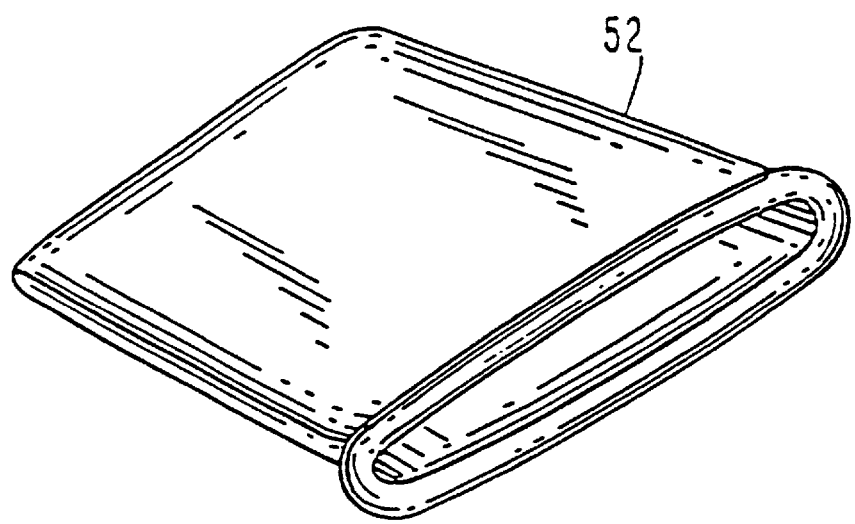
FIG. 18 is a perspective view of a condom within the condom dispenser as in FIG. 17.

For added convenience, as shown in FIGS. 17–18, condom package 50 may be short. In this case it would be used to dispense a rolled or folded condom 52a which would be unrolled or unfolded as needed.

In other respects, this further embodiment of the present invention for condoms differs only in that condom shaped package dispenser 50 is used, with or without a partially elongated receptacle tip end 55, depending upon the shape of each of condoms 52a, 52b . . . 52z etc. Therefore, when condom package dispenser 50 is opened as shown in FIG. 16, condom package dispenser 50 maintains equal expansion of all surfaces of each of condoms 52a, 52b . . . 52z etc, including partially elongated receptacle tips 56a, 56b . . . 56z etc, so that innermost condom 52a can be held in the proper position for placement. The proximal open end portions 54 of the plurality of condoms 52a, 52b . . . 52z are stretched over a collar portion 57 of condom package dispenser 50, and condoms 52a, 52b . . . 52z etc. are maintained in an expanded state, wherein the user first removes innermost protective leak-proof layer 53a, thereby exposing innermost condom 52a, and inserts the penis into innermost condom 52a, and a release tab is pulled, so that condom 52a deflates over the skin in a tight fitting manner, leaving next a leak-proof layer 53b inside next innermost condom 52b.

Moreover, the inside shape of condom dispensing package 50 may be condom shaped, or the plurality of condoms may be inserted in an outermost condom shaped layer made of a nonelastic material, such as Mylar®, similar to the glove embodiment described in FIGS. 6 and 7.

Figure 19:
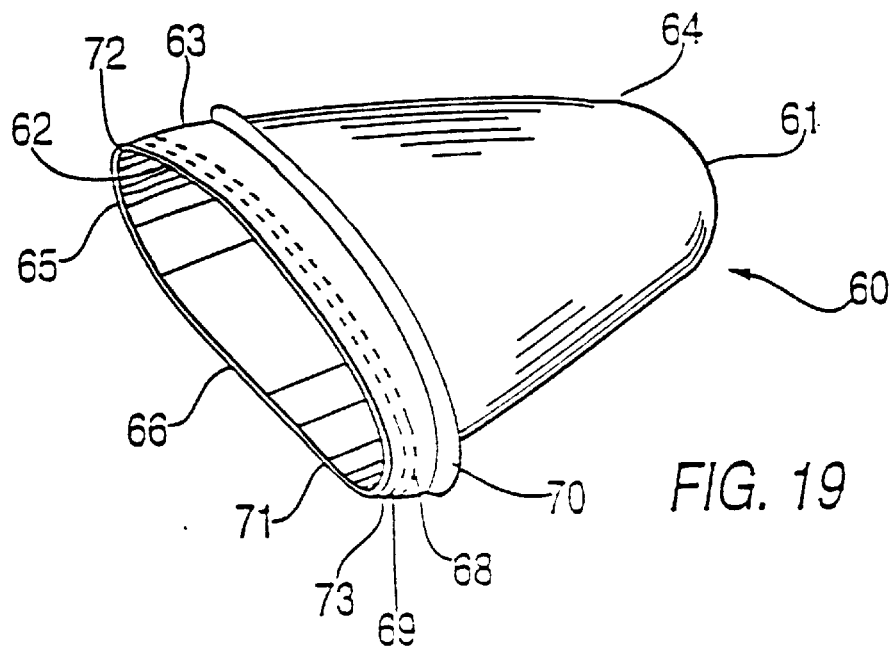
FIG. 19 is a perspective view of a tapered multi-condom package.

A compact condom dispenser package 60 as shown in FIG. 19 contains a number of condoms 62 nested with interleaved separators 63 which form a hermetic seal around each condom 62.

Quantities such as one to twelve condoms 62 can be packaged in this manner.

Figure 20:
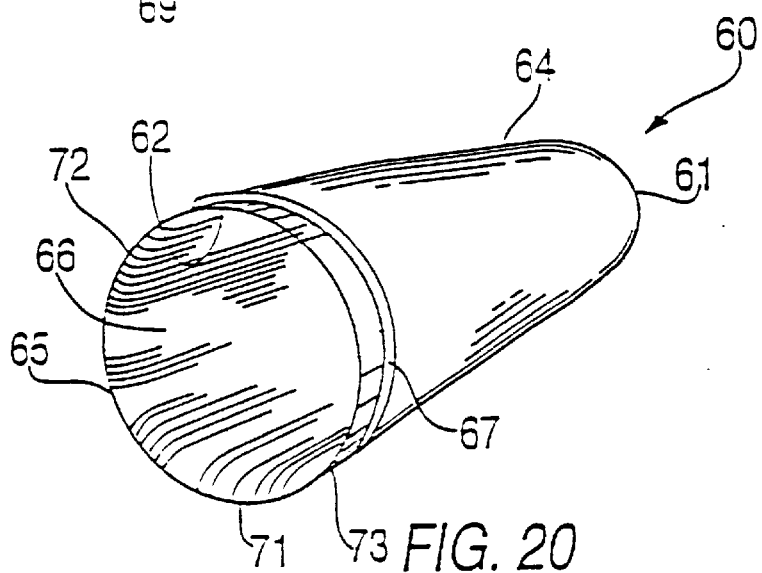
FIG. 20 is a perspective view of the condom package as in FIG. 19.

The length of package dispenser 60 is reduced by packaging condoms 62 in a partially rolled-up configuration. Condoms 62 are contained in a tapered plastic outer shell 64 with the partially rolled open ends folded over the lip 65 of outer shell 64. Outer shell 64 folds fairly flat as shown with the proximal end 66 in a flattened oval configuration. Distal end 61 is closed. A molded flange 67 encircling outer shell 64 near proximal open end 66 forms a convenient surface for attaching separators 63 thereto and providing a sealed surface 70 thereat. Separators 63 can be heat sealed, adhesively bonded, ultrasonically bonded or otherwise attached to each other and to flange 67 in such a manner as to achieve a hermetic seal. A tear strip 68 is provided with an end tab 69 and is torn open to remove innermost separator layer 63 and to expose both the inner condom surface of condom 62 as well as the rolled open condom end 71 on the lip 65 of package shell 64. As shown in FIG. 20, by pressing in on the edges 72, 73 forming the major axis of the oval opening 66 shown in FIG. 19, the package dispenser 60 assumes the open shape shown in FIG. 20. Package dispenser 60 is now ready for donning. This is easily accomplished by placing package dispenser 60 over the front portion of the erect penis and sliding rolled condom end 71 off the package dispenser lip 65 and onto the penis. The donning process is completed by further rolling of the condom 62 down the shaft of the penis.

Figure 21:
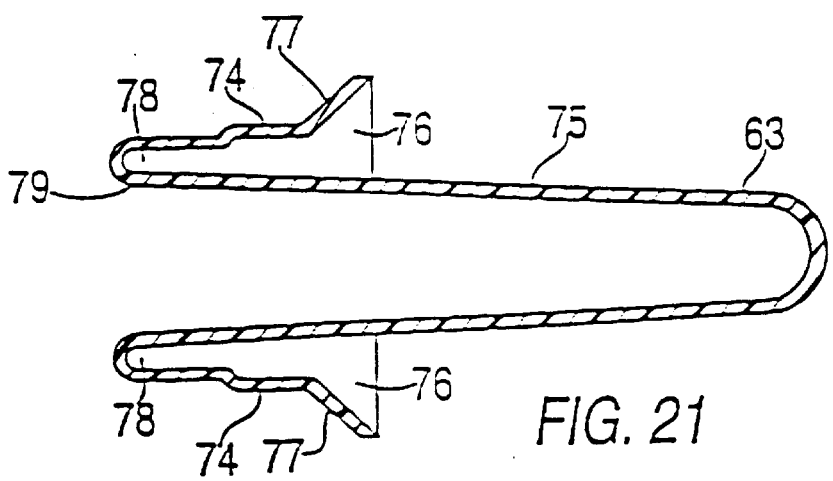
FIG. 21 is a cross-sectional side view of a typical preformed separator of the condom package as in FIG. 19.

FIG. 21 shows a side view cross-section of a typical preformed separator layer 63 as used between condoms 62. Separator layer 63 can be of a variety of materials that are impermeable to air. They do not have to be elastomeric, but they do have to be somewhat flexible so as to go from the flattened configuration as in FIG. 19 to the round cross-section configuration of FIG. 20.

Materials that can be used for separator layer 63 include a wide variety such as Mylar™ or Aclar, a very low permeability material. Laminates may also be used for this application. One example is a low density polyethylene (LDPE) substrate laminated to an aluminum foil layer as a permeability barrier. The LDPE substrate also serves as the heat bonding agent. The preforms are preferably vacuum formed, pressure formed or injection molded as appropriate to the particular material. Tear strip 68 is integrated into separators 63 in the general location region shown. Tear strip region 74 ends cantilevered in spaced relation above body portion 75 of separator layer 63, so that a clearance recess 76 is formed between body portion 75 and tear strip region 74, which has extending therefrom a flared attachment surface 77 for the next subsequent separator 63. The recesses 76 have clearances which are more understandable in FIG. 22.

A smaller recess 78 is provided between an open end 79 of separator 63 and tear strip region 74 to provide clearance for insertion of package shell 64 therein. The length of the package shell recess 78 as well as the rolled condom recess 76 will depend on the particular location of the separator 63 and the number of condoms 62 in the package dispenser 60.

The tapered form of outer shell 64 as well as separators 63, facilitates simple automated loading and assembly by using a tapered cylindrical mandrel. The shape also enhances the separability of condoms 62 from the package dispenser during donning. Each condom 62 is placed on the mandrel "M", and then a separator 63 is placed on the mandrel "M". The condom 62 is held on the mandrel "M" by rolls "R" or other means. Then the mandrel "M" is inserted in the pack with the exception of rolled edge 71 of condom 62, which rolls down the tapered end of the mandrel "M", and the rolled edge 71 is stopped by flange 67 of the package dispenser 60.

Then the separator 63 is placed on the mandrel "M", which is bonded to shell 64. Separators 63 are bonded to shell 64 sequentially, or using other packaging machinery. All condoms 62 can be assembled on the mandrel "M" and separator layers 63 can be bonded in one final step.

FIGS. 21A, 21B, 21C, 21D and 21E illustrate a sequential method that can be used to assemble the multi-condom package 60. FIG. 21A shows tapered cylindrical mandrel "M" with the first condom 62, placed over it and an array of rollers "R" (two shown) around the circumference of the condom lip moving to the left, urging the condom 62 to unroll to the proper length. Alternate structures such as pliable fingers or bristles from a circular brush structure can be used instead of the rollers "R". The condom rollers "R" are spread away from the surface and moved further to the left beyond the condom rolled edge (not shown).

Then the package shell 64 is placed over the condom 62 on the mandrel "M" and the rollers "R" are then moved to the right urging the condom edge over the lip of the package shell 64 toward the sealing flange, as shown in FIG. 21B. After this step, the condom/shell 62, 64 is withdrawn off the mandrel "M" preferably with the help of a blast of compressed air through a hole or holes in the mandrel (not shown).

The first separator 63 is placed over the mandrel "M" as shown in FIG. 21C. Then the condom-shell assembly 62, 64 is placed over the separator 63, which had been placed over the mandrel "M" as shown in FIG. 21D. At this point, a heat seal ring "S" is moved to the right so as to contact the edge of the first separator 63 and apply heat and pressure to hermetically seal it to the sealing flange 67 of the package shell 64.

Now the sealed subassembly (separator/condom/shell) is removed from the mandrel (not shown). For the rest of the condom package assembly, the steps discussed are essentially repeated with FIG. 21E showing the unrolling of a second condom.

Figure 22:
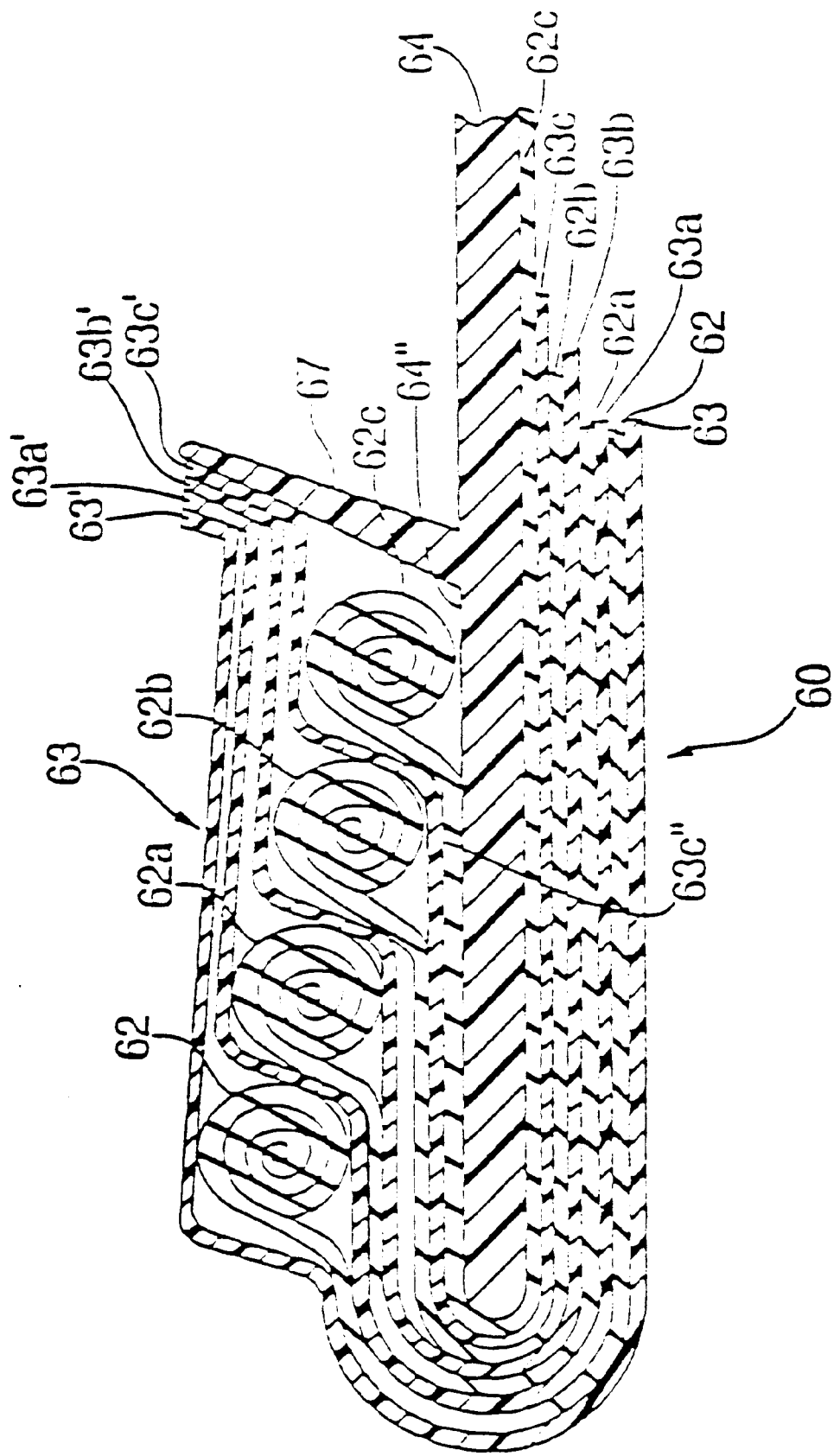
FIG. 22 is a closeup cross-sectional side view of lip portion of package as in FIG. 19.

FIG. 22 is a detail of the lip portion of the package dispenser 60 in cross-section, with the package shell 64 shown with sealing flange 67. Also shown is each layer of condom 62, 62a, 62c, etc. Separators 63, 63a, 63b, etc. are shown with the sealed ends 63' 63a', 63b', 63c' at sealing flange 67. While FIG. 22 shows a four condom package, it is merely illustrative, as the amount of condoms 62 and separators 63 may be varied.

Figure 23:
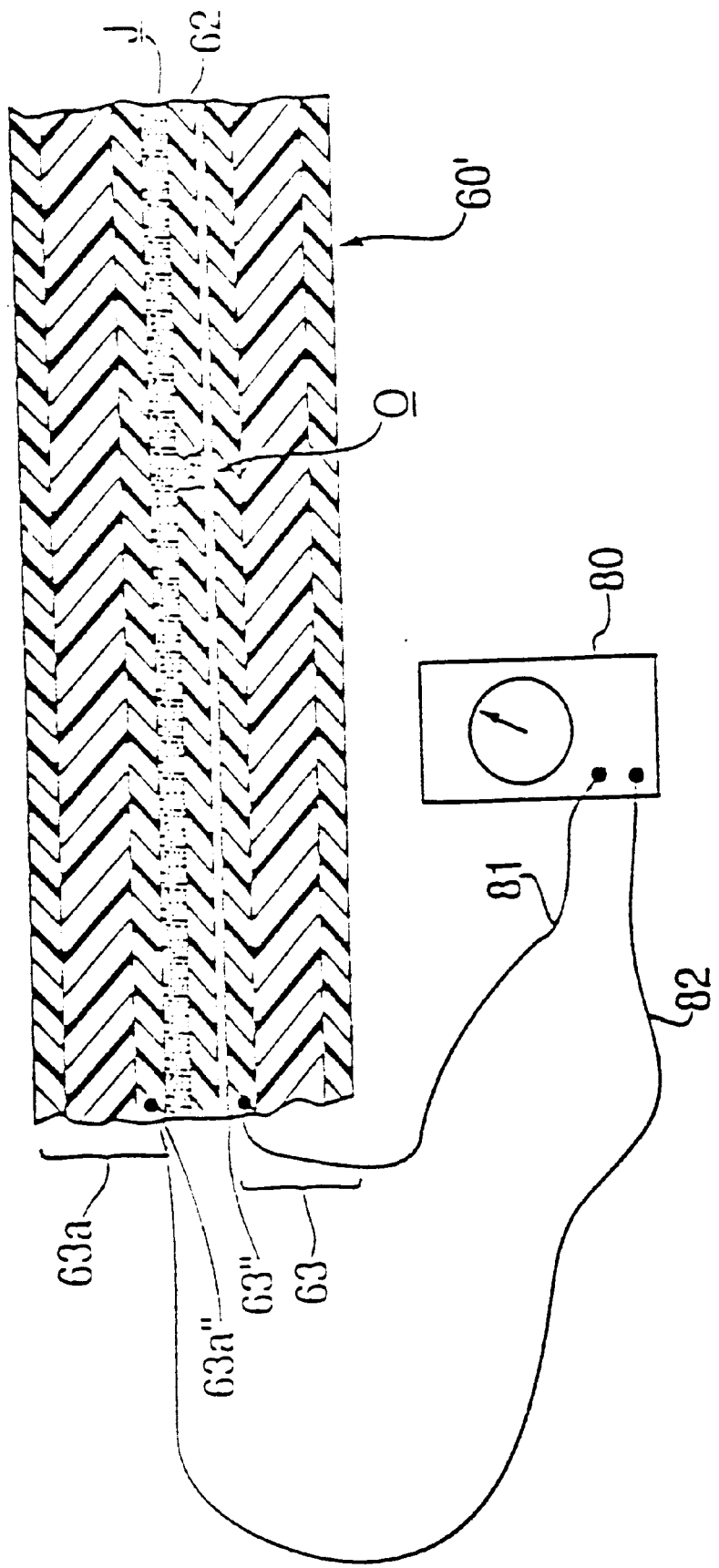
FIG. 23 is a side elevational view of a condom integrity testing procedure for the condom package as in FIG. 19.

As shown in FIG. 23, through the use of conductive polymers such as those recently developed for the electronics industry, or laminates with conductive surfaces for separators 63, 63a, 63b, 63c, etc. some condom integrity testing of condoms 62, 62a, 62b, 62c, etc. can be performed after insertion in package dispenser 60', but prior to sealing of the separator ends 63, 63a, 63b, 63c, etc.. This operation can be automated with ohmmeter 80 connected by leads 81, 82 connected to respective conductive layers 63a, 63a' attached to separators 63, 63b. The operation simply tests the continuity or resistance between two consecutive separator layers 63, 63a, etc. to assess the integrity of the condom 62 in between. Condom 62, an insulator, preferably results in an infinite, or very high, resistance reading. For a dry condom, this reading may not pick up small flaws such as pinholes because the thickness of the condom material may keep the separator layers 63, 63a apart. However, if condom 62 is lubricated and/or contains spermicide on its outer surface, the jelly material "J" may be made somewhat conductive. The jelly material used may tend to leak through small openings "O" in the wall of condom 62 as shown in FIG. 23.

In this case, the electrical integrity testing may be far more robust, showing minor flaws that would escape in a dry condom test. The test of the final condom in the stack shown in FIG. 22, is preferably between conductive layer 63c" of last separator 63c and conductive inner surface 64" of outer plastic shell 64.

Figure 24:
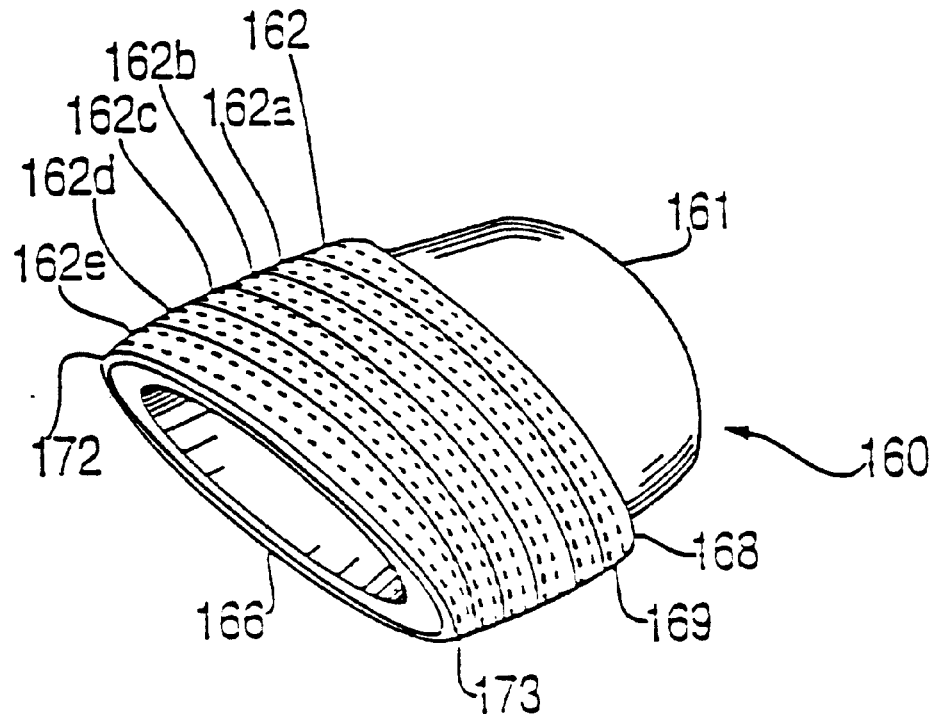
FIG. 24 is a perspective view of an alternate package dispenser for condoms.

FIG. 24 shows a separable package dispenser 160 for six condom subpackages 162, 162a, 162b, 162c, 162d, 162e, with as few as one packaged condom 62, or larger packages having up to perhaps a dozen or more condoms 62, 62a, 62b, etc. Package dispenser 160 can be used in much the same manner as the tapered multi-condom package if the condoms 62, 62a, 62b, etc. are just used sequentially as purchased.

However, alternately as shown in FIG. 24–27, these separable packages 160 can be separated into multiple subpackages of one or more condoms.

Figure 25:
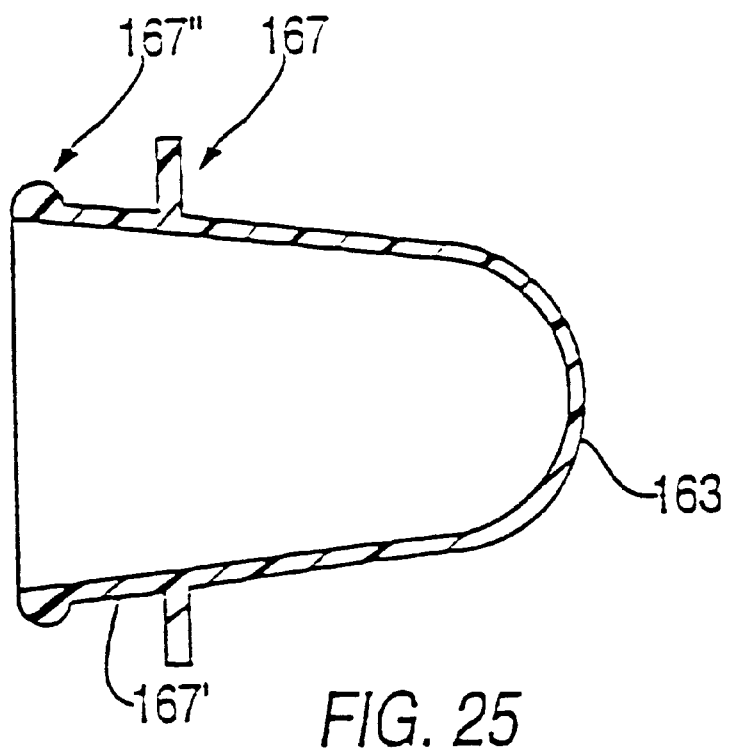
FIG. 25 is a side cross-sectional view of the dispenser as in FIG. 24.

Although basically a flattened oval tapered packaging concept like the multi condom version, one major difference with package dispenser 160 is the absence of a thick plastic outer shell. The role of this shell is assumed by multiple semi-rigid impervious plastic or laminated separators 163, 163a, 163b, 163c, etc. which have the dual role of being inter-condom separators as well as being support vehicles for condoms 62, 62a, 62b, etc. To use a condom 62, the pull tab 169 as shown in FIG. 24, nearest the closed distal end 161 is pulled to operate the tear strip 168 which then reveals the rolled condom end on the separator rim. FIG. 25 shows a side view cross-section of a semi-rigid separator 163 with an annular seal chamber wall flange 167. The portion in front of the seal chamber wall flange 167 is an extension 167 with an annular bermed condom rim 167" retainer to support the rolled open end of condom 62.

Figure 26:
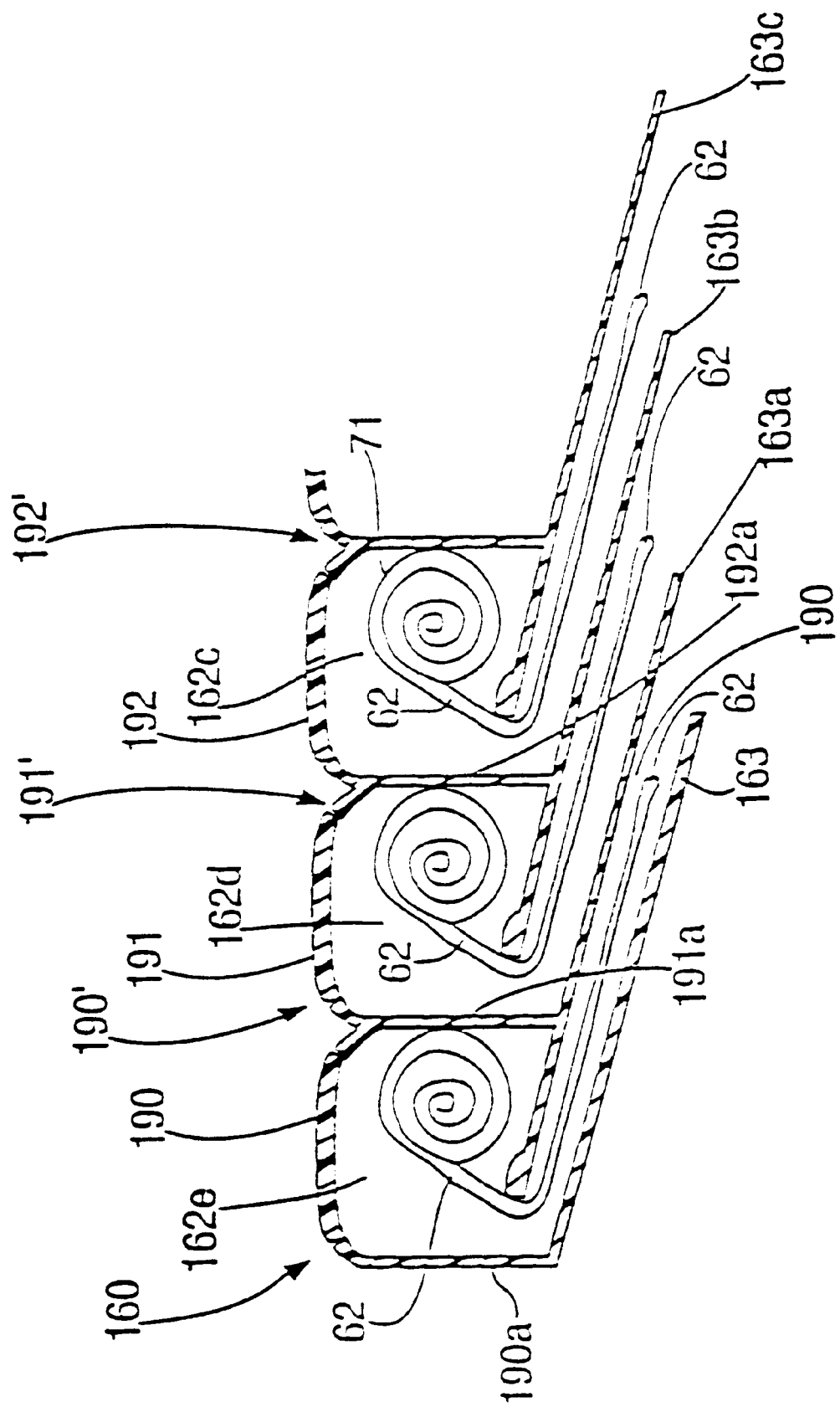
FIG. 26 is a closeup cross-sectional view of the condom as in FIG. 24.

FIG. 26 is a detail illustration of the last three seal chambers 162e, 162d, 162c near the edge of opening 166 of package dispenser 160. Condoms 62 are sealed between two adjacent separators 163b, 163c or between the end seal 163 and an adjacent separator 163a. A small gas space 190 is permitted between the outer wall of the condom 62 and the inner edge of the next separator 163a. A small amount of air or dry nitrogen may be admitted at assembly so that donning would become a more automatic procedure. With a small amount of gas in the space 190, when the package dispenser 160 is urged into a shape having a round cross-section by applying pressure on the sides edges 172, 173 and the tip of the erect penis is inserted in the opening 166, the increased gas pressure between condom 62 wall and separator 163a causes the rolled end of the condom 62 to expand off separator lip automatically onto the penile shaft. The use of nitrogen instead of air reduces the chance of latex oxidation.

Each condom 62 is covered by chamber caps 190, 191, 192, etc., which are rings of impermeable plastic that are sealed to the seal chamber walls 190a, 191a, 192a of separators 163a, 163b, 163c or the end seal 163. Caps 190, 191, 192, etc. have molded-in notches 190', 191', 192' which act as tear strips revealing the condom edge when removed. A subpackage 162 may be separated at any location by removing the associated tear strip 168, to separate subpackage 162 into two sections, a front and a back section.

Figure 27:
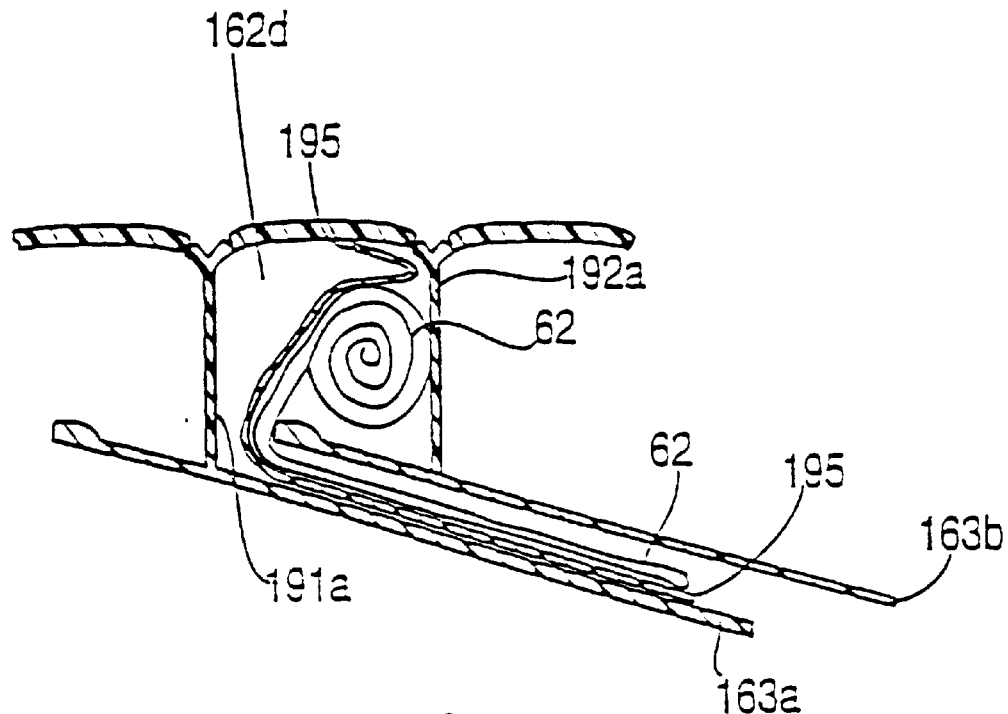
FIG. 27 is a closeup cross-sectional view of the seal chamber detail of a further alternate embodiment of a condom dispenser.

While the rear section is still hermetically sealed, the end condom 62 on the front section has an inner surface and edge that is exposed to the ambient air. If it is to be used in the immediate future, there is no problem. However, if it is carried or stored for a long time, it may get contaminated or deteriorate through oxidation. FIG. 27 shows the addition of a thin barrier film 195 to mitigate these problems. While not offering a true hermetic seal to the inner surface and edge as thin films are somewhat permeable, the protective layer helps. Film 195 is removed prior to donning by grasping the end thereof and peeling it off the wall wherein pressure sensitive adhesive with limited peel strength is used.

Figure 28:
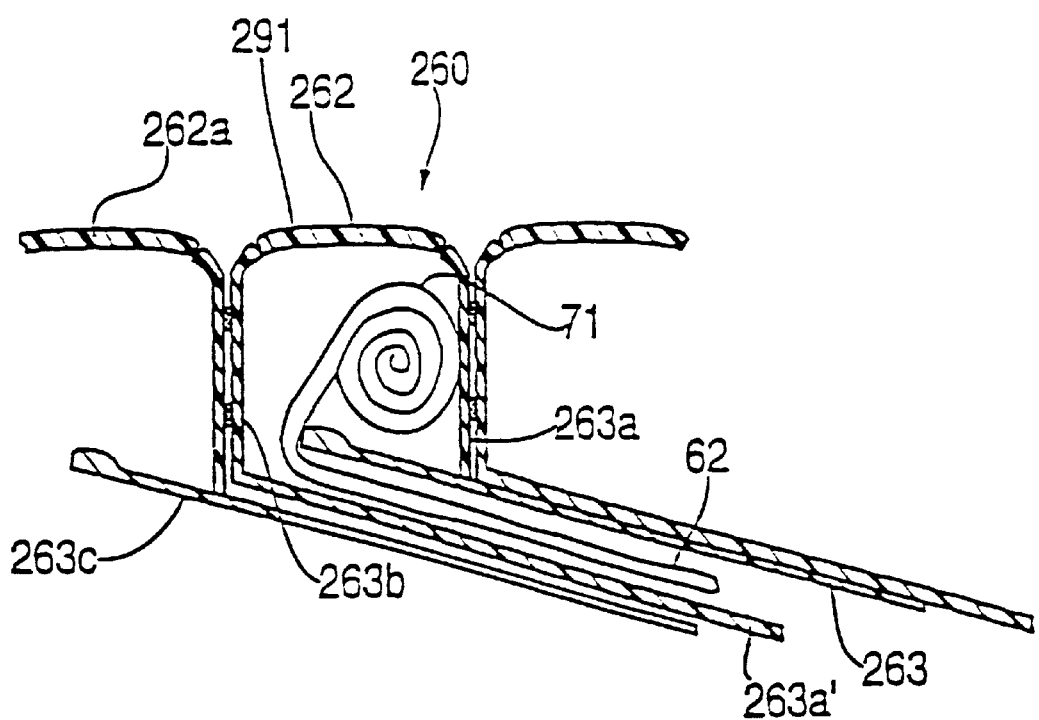
FIG. 28 is a closeup view of a further alternate condom dispenser.
Figure 30:
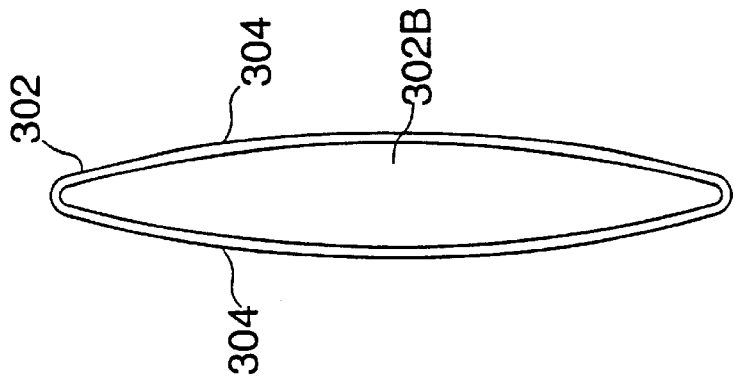
FIG. 30 is a cross sectional end view of the dispenser as in FIG. 29.
Figure 29:
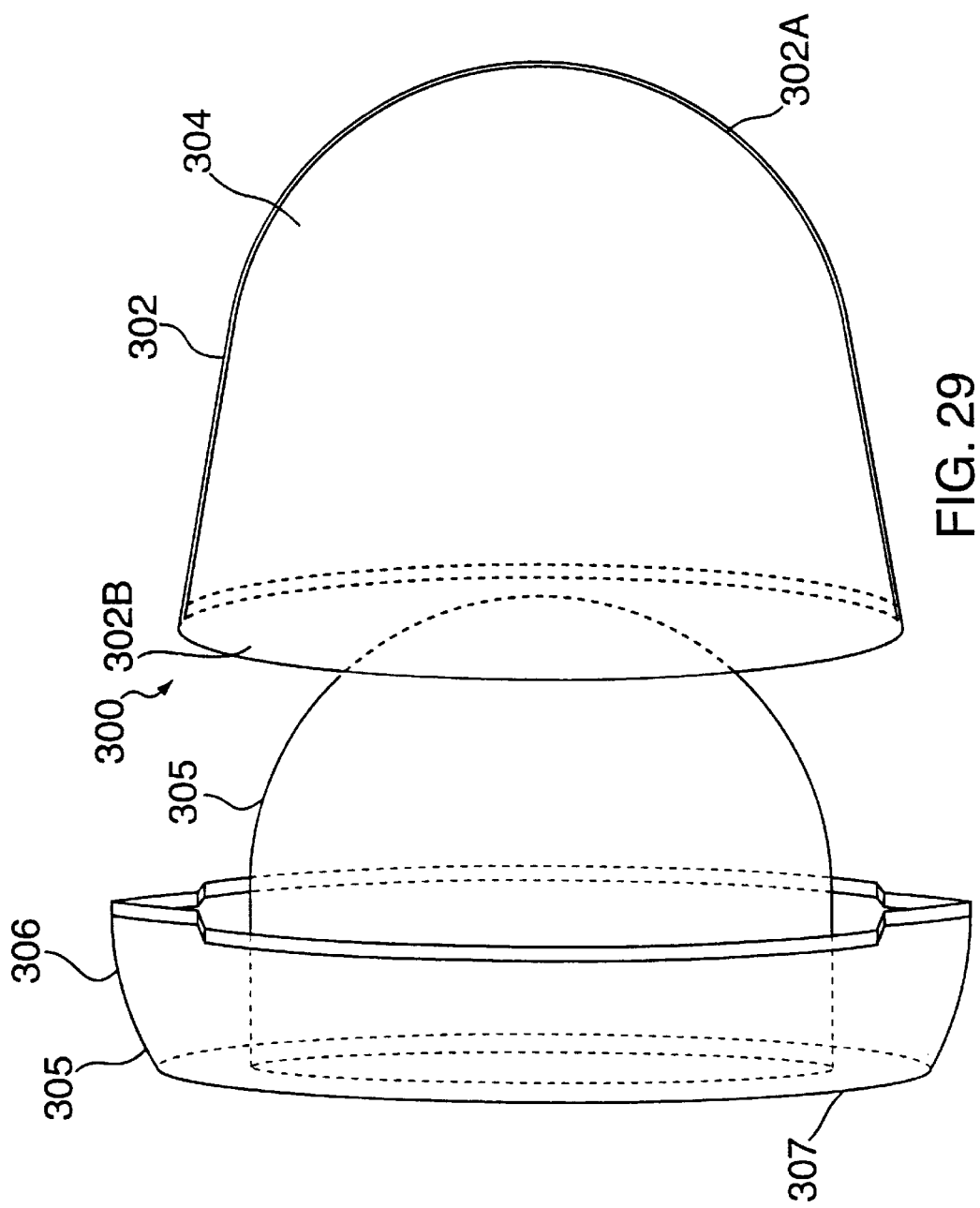
FIG. 29 is an exploded perspective of a further embodiment for a condom dispenser including a cap closure having a projecting condom holding plate insertable within the condom within the dispenser.

FIG. 28 shows yet another embodiment for a separable package 260. Another embodiment provides a plurality of individually sealed single condom packages in a partially unrolled state to facilate donning, which packages are removeable from each other by a tear seal. Accordingly, the user can carry a single condom package 260 if they so wish.

This embodiment 260 uses double layer separators 263a, or 263b, 263c, between adjacent condoms 62. One separator is shaped exactly as shown in FIG. 25 without the condom support portion. These separators 262a, 262b, etc. may be somewhat thinner than the single versions. A cap 291 is used to form a hermetic seal encasing a condom 62 between a "short" separator 263a and a "full" separator 263a'. Each sealed condom subassembly 262 nests with the next one 262a forming a complete multi-condom separable package by "spot" bonding between subassemblies 262, 262a with a low strength adhesive. To separate a package into a smaller one, it is just physically separated by breaking apart and the tear strip is not used. In this manner, all condoms 62 remain hermetically sealed until used even if the large package is separated into smaller units. Even a single condom can be separated and remains sealed.

In a further embodiment shown in FIGS. 29–34, a package 300 dispenses a single condom 301 directly on a penis. The package 300 includes a container 302 having the elongated shape of a condom 301 closed at one end 302a and open at another end 302b. The container 302 has outside wall 304 and is made of a flexible material permitting the container 302 to be flattened. The container 302 includes a flattened closure cap 300 insertable over the open end 305 of the container 302. Projecting from the inside of the closure cap 303 is a condom holder plate 305 insertable within the condom.

Figure 31:
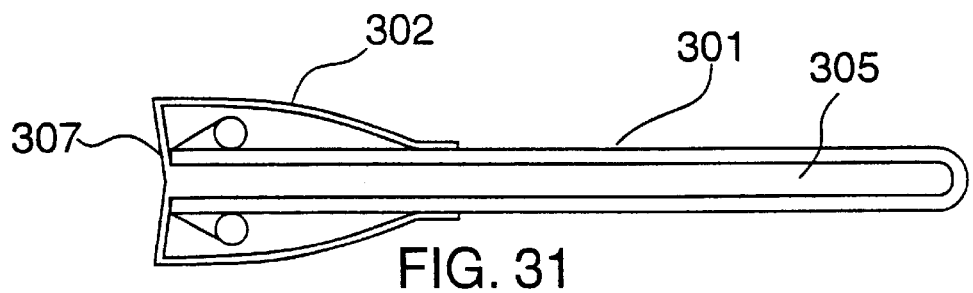
FIG. 31 is a left side elevational view in cross section of the dispenser as in FIG. 29, shown in a closed position.
Figure 32:
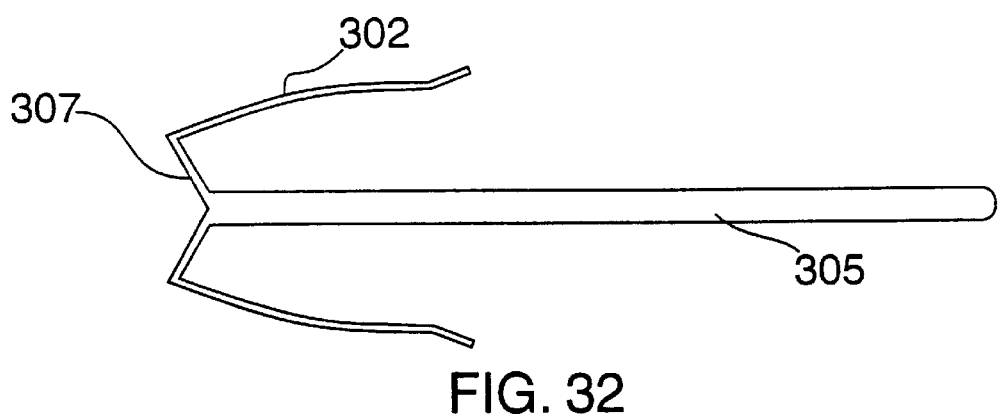
FIG. 32 is a left side elevational view in cross section of the dispenser as in FIG. 29, shown in an open position.
Figure 33:
FIG. 33 is a left side elevational view in cross section of a condom shown mounted upon the condom holding plate of the dispenser as in FIG. 29; and, FIG. 34 is a left side elevational view in cross section of the pouch portion of the dispenser as in FIG. 29 shown open and empty.
Figure 34:
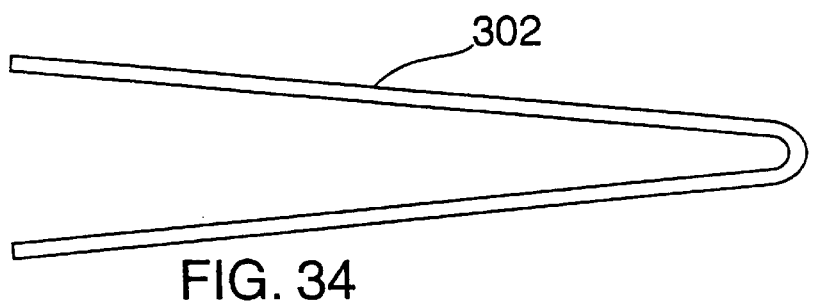
Figure 36D:
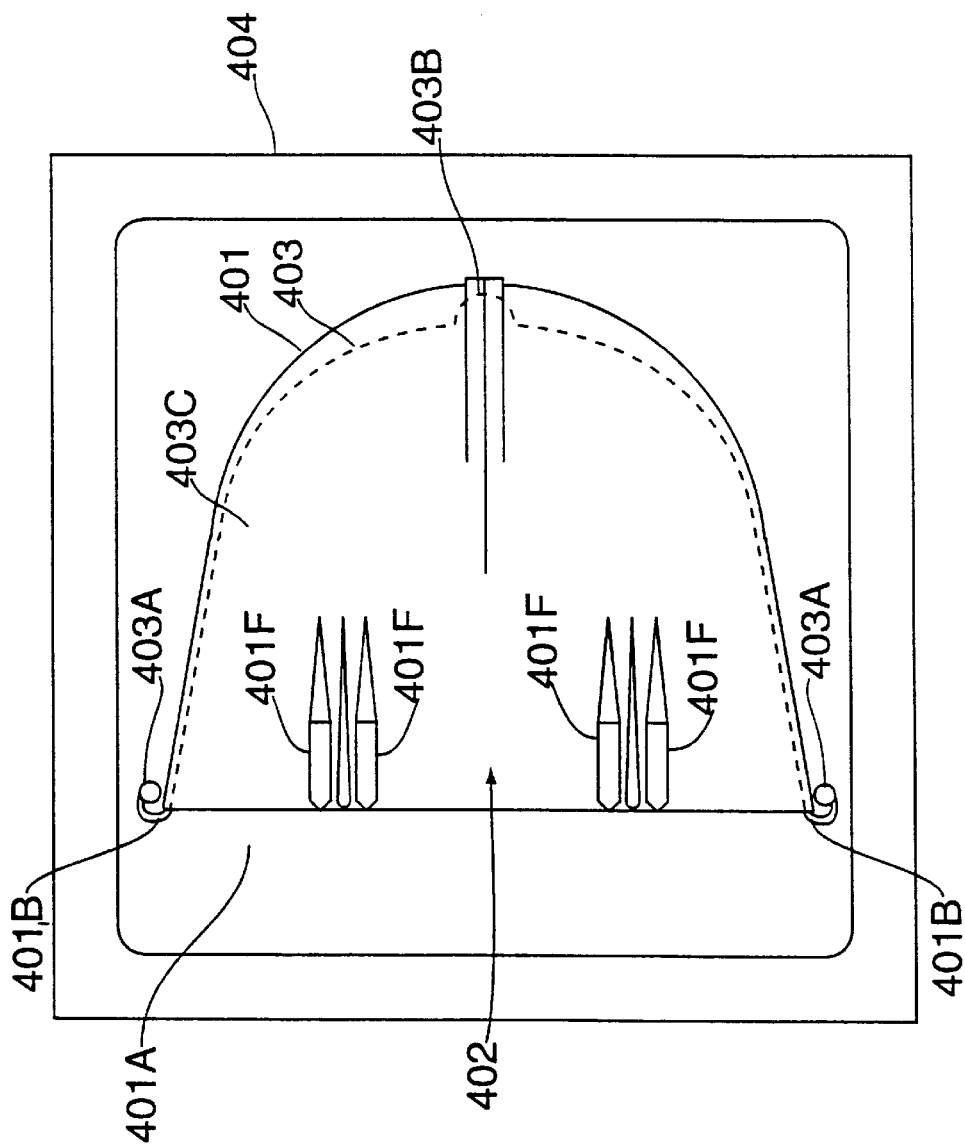
FIG. 36D shows the pouch package within a sealed, openable outer envelope container.

As shown in FIGS. 31 and 32, the closure cap 305 includes an annular ring member 306 which includes a snap hinge 307 to enable the closure cap 305 to spring open as in FIG. 32.

The container 302 has a lip forming the open end 302b thereof and a flange encircling the container 302 adjacent to the open end 302b.

While the package 300 can be made without separator seals, preferably as in the embodiments shown in FIGS. 19–23, a first separator (not shown in FIGS. 29–34) conforms to and lines the inside of the container 302 with the separator having an open end and stretched over a flange for achieving a hermetic seal within the container 302. The first separator has a tear strip on the outside adjacent the flange for providing tearing of the first separator.

A single 301 condom within the container 302 lines the inside of the first separator, with the open end of the condom 301 rolled over the first separator and the flange leaves the tear strip exposed.

A second separator (not shown in FIGS. 29–34) lines the inside wall of the condom 301 with the open end of the second separator rolled over the condom and the separator on the flange to achieve hermetic sealing of the condom 301, so that removal of the second separator permits the penis to be inserted into the condom 301 and pulling of the tear strip unseals the condom 301 from the first separator, resulting in the condom 301 being released so that the penis can withdraw from the container 302 and the first separator with the condom 301 on the penis.

The container 302 with the condom 301 and separators therein is normally flattened for convenient storage and is enlargeable to the shape of a penis when said condom 301 is to be dispensed on a penis by applying force on the edges of the container 302, wherein the edges conform to the major axis of the open end of the container 302.

The dispenser may be foreshortened so that the condom therein is partially unrolled on the outside of the container, thus achieving a compact dispenser.

In another embodiment, the dispenser shown in FIGS. 29–34 can be used for a plurality of condoms.

A first condom is located within the container lining the inside of the first separator, with the open end of the first condom rolled over the first separator and the flange leaving said first tear stip means exposed.

A second condom is also located within the container lining the inside of the second separator, with the open end of the second condom rolled over the first separator, the first condom, and the second separator leaving the first and second tear strip means exposed.

A third separator lines the inside wall of the second condom with the open end of the third separator rolled over the first and second condoms and the separators on the flange, achieving hermetic sealing of the second condom and leaving the tear stip means exposed, so that removal of the third separator permits the penis to be inserted into the second condom and pulling of the second tear strip unseals the second condom from the second separator, resulting in the condom being released so that the penis can withdraw with the second condom on the penis.

The container with the interleaved condoms and the separators therein is normally flattened for convenient storage and enlargeable to the shape of a penis when the condoms are to be dispensed.

As shown in FIGS. 35, 35A, 35B, 35C, 36, 36A, 36B and 36C a further embodiment includes pouch package 401 in the shape of a hollow container, having hollow interior 402, for insertion of a condom 403 partially unrolled therein.

In that manner, when pouch package 401 is removed from sealed, openable outer envelope container 404 (shown in FIG. 36D) by tearing or otherwise, open end 401*a* of pouch package 401 exposes rolled open end 403*a* of condom 403 for donning upon a penis.

Closed end 403*b* of condom 403 nests within pouch package 401. However, the unrolled portion 403*c* of condom 403 is long enough for insertion of the tip of the penis therein.

When in place upon the tip of the penis, rolled open end 403*a* of condom 403 is then unrolled off of pouch package 401 and down onto the shaft of the penis.

Pouch package 401 includes condom retaining means a member 401*b*, such as a peripherally extending lip thereat, for wrapping of the open end 403*a* of condom 403 therearound.

Pouch package 401 comprises two convex arcuate walls 401*c*' and 401*d*', each partially co-joined at corner joints 401*c*, 401*d* of pouch package 401, when viewed in an end view as in FIGS. 35 and 36. Corner joints 401*c* and 401*d* extend along the closed periphery of pouch package 401, except at open end 401*a* thereof.

Thereafter, elongated opening 401*a* becomes rounder by manually pinching joints 401*c* and 401*d* toward each other, resulting in the rounder open position of walls 401*c*' and 401*d*' of pouch package 401, as shown in FIGS. 35C and 36C. Arrows I—I in FIG. 35 indicate the direction of pinching of joints 401*c*, 401*d*. Arrows II—II in FIGS. 35C and 36C indicate the expansion movement of walls 401*c*' and 401*d*' of pouch package 401 at mid point 401*e* thereof.

As further shown in FIGS. 35B, 36B, 37 and 38, one or more supports 401*f*, such as axially extending ridges or otherwise, release trapped air caused by containment of the partially rolled portion 403*a* of latex condom 403 over lip edge 401*b* of pouch package 401. These supports 401*f* are preferred but optional.

In summary, FIGS. 35, 35A, 35B and 35C all disclose a preferred embodiment for a package 401 for accommodating a condom 403 therein in an open position for donning upon a penis.

It is further noted that other modifications may be made to the present invention, without departing from the spirit and scope of the present invention, as noted in the appended claims.

What is claimed is:

1. A pouch package for dispensing of a condom directly on a penis comprising:

a hollow container formed of two walls and corner joints, said corner joints co-joining said two walls to form a flat configuration, said hollow container being made of a flexible material which allows said corner joints to be pinched toward each other to urge said hollow container toward an open configuration, said hollow container having an elongated shape, said hollow container being closed at one end and open at another end; and a condom at least partially disposed inside said hollow container, said condom having a condom tip extending to said closed end;

said hollow container having an inside wall configuration conforming to an exterior shape of said condom, wherein said closed end of said container is adapted to nest said tip therein;

said hollow container having a condom retaining member that retains said condom within said hollow container;

said hollow container being formed with ridges which allow air to escape from the package.

2. The pouch package for dispensing of a condom directly upon a penis as in claim 1 wherein said condom retaining member comprises a lip edge around a periphery of said open end of said hollow container.

3. The pouch package for dispensing a condom directly on a penis as in claim 2 wherein said condom is arranged within said hollow containers with said condom lining said hollow interior of said container, with an open end of said condom rolled over said lip edge, leaving a rolled up portion of said condom exposed;

said container with said condom therein normally being flattened for convenient storage and being enlargeable to the shape of a penis when said container is in said open configuration so that said condom can be dispensed on a penis.

4. The package as in claim 3 wherein said container is enlargeable to the shape of a penis by pinching of co-joined edges thereof toward a mid point of two partially co-joined walls of said container.

5. The package of claim 1 in which said container is foreshortened so that the condom therein is partially unrolled on the outside of said container.

6. The package of claim 1 wherein said container holds only a single condom having its tip in contact with said closed end.

* * * * *